United States Patent
Shishilla et al.

(10) Patent No.: US 11,517,752 B2
(45) Date of Patent: *Dec. 6, 2022

(54) TRIAL STIMULATION SYSTEMS

(71) Applicant: MEDTRONIC, INC., Minneapolis, MN (US)

(72) Inventors: John Shishilla, Medina, MN (US); Kathryn Pederson, East Bethel, MN (US); Mukul Jain, Boyds, MD (US); Nicholas S. Mairs, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/751,906

(22) Filed: May 24, 2022

(65) Prior Publication Data
US 2022/0280790 A1    Sep. 8, 2022

Related U.S. Application Data

(63) Continuation of application No. 16/530,636, filed on Aug. 2, 2019, now Pat. No. 11,376,429, which is a (Continued)

(51) Int. Cl.
*A61N 1/36*    (2006.01)
*A61N 1/372*    (2006.01)
*A61N 1/05*    (2006.01)

(52) U.S. Cl.
CPC ..... *A61N 1/36017* (2013.01); *A61N 1/36128* (2013.01); *A61N 1/36142* (2013.01); (Continued)

(58) Field of Classification Search
CPC ............ A61N 1/36017; A61N 1/36128; A61N 1/36142; A61N 1/37247; A61N 1/0502; (Continued)

(56) References Cited

U.S. PATENT DOCUMENTS 4,979,517 A    12/1990    Grossman et al.
5,304,206 A    4/1994    Baker, Jr. et al.
(Continued)

FOREIGN PATENT DOCUMENTS

WO    0209808 A1    2/2002

OTHER PUBLICATIONS

Patient Trial Handbook: Precision Spinal Cord Stimulation System, Advanced Bionics, Part No. 9055426-001 Rev A, 2006, 76 pages.
(Continued)

*Primary Examiner* — Mallika D Fairchild
(74) *Attorney, Agent, or Firm* — Fredrikson & Byron, P.A.

(57) ABSTRACT

A trial stimulation system includes a trial electrical stimulator. Additionally, systems for securing a disposable trial stimulator to the body of a patient are described, which may function to improve the durability of the system during the trial period and reduce the risk of damage or malfunction to the system due to lead/electrode dislocation and/or off-label uses like showering or bathing with the trial stimulator still secured to the body.

40 Claims, 10 Drawing Sheets

Related U.S. Application Data continuation of application No. 14/396,659, filed as application No. PCT/US2013/029273 on Mar. 6, 2013, now Pat. No. 10,369,370.

(60) Provisional application No. 61/638,933, filed on Apr. 26, 2012.

(52) U.S. Cl.
CPC ........ *A61N 1/37247* (2013.01); *A61N 1/0502* (2013.01); *A61N 1/36021* (2013.01); *A61N 1/36025* (2013.01); *A61N 1/37235* (2013.01)

(58) Field of Classification Search
CPC ............ A61N 1/36021; A61N 1/36025; A61N 1/37235
See application file for complete search history.

(56) References Cited

U.S. PATENT DOCUMENTS

| | | | |
|---|---|---|---|
| 5,330,515 A | 7/1994 | Rutecki et al. | |
| 5,374,279 A | 12/1994 | Duffin, Jr. et al. | |
| 5,386,084 A | 1/1995 | Risko | |
| 5,518,155 A | 5/1996 | Gallagher | |
| 5,669,790 A | 9/1997 | Carson et al. | |
| 6,065,154 A | 5/2000 | Hulings et al. | |
| 6,205,359 B1 | 3/2001 | Boveja | |
| 6,249,703 B1 | 6/2001 | Stanton et al. | |
| 6,282,448 B1 | 8/2001 | Katz et al. | |
| 6,366,814 B1 | 4/2002 | Boveja et al. | |
| 6,505,074 B2 | 1/2003 | Boveja et al. | |
| 6,521,309 B1 | 2/2003 | Chen et al. | |
| 6,687,538 B1* | 2/2004 | Hrdlicka ............ | A61N 1/36014 607/2 |
| 6,687,543 B1 | 2/2004 | Isaac | |
| 6,895,280 B2 | 5/2005 | Meadows et al. | |
| 7,120,499 B2 | 10/2006 | Thrope et al. | |
| 7,177,703 B2 | 2/2007 | Boveja et al. | |
| 7,263,405 B2 | 8/2007 | Boveja et al. | |
| 7,330,762 B2 | 2/2008 | Boveja et al. | |
| 7,359,751 B1 | 4/2008 | Erickson et al. | |
| 7,643,880 B2 | 1/2010 | Tanagho et al. | |
| 7,680,540 B2 | 3/2010 | Jensen et al. | |
| 7,937,158 B2 | 5/2011 | Erickson et al. | |
| 8,483,836 B2 | 7/2013 | Polefko et al. | |
| 8,571,687 B2 | 10/2013 | Libbus et al. | |
| 8,634,932 B1* | 1/2014 | Ye ........................ | A61N 1/0558 607/116 |
| 8,825,153 B2 | 9/2014 | Kokones et al. | |
| 8,938,303 B1 | 1/2015 | Matsen | |
| 9,248,293 B2 | 2/2016 | Walker et al. | |
| 9,259,574 B2 | 2/2016 | Aghassian et al. | |
| 9,446,241 B2 | 9/2016 | Lee | |
| 9,498,633 B2 | 11/2016 | Laing et al. | |
| 9,707,405 B2 | 7/2017 | Shishilla et al. | |
| 9,724,513 B2 | 8/2017 | Lane et al. | |
| 9,861,822 B2 | 1/2018 | Trier et al. | |
| 9,878,168 B2 | 1/2018 | Shishilla et al. | |
| 10,092,762 B2 | 10/2018 | Jiang et al. | |
| 10,195,423 B2 | 2/2019 | Jiang et al. | |
| 10,369,370 B2 | 8/2019 | Shishilla et al. | |
| 10,537,741 B2 | 1/2020 | Bradley et al. | |
| 10,668,285 B2 | 6/2020 | Boggs | |
| 2002/0143376 A1 | 10/2002 | Chinn | |
| 2003/0018369 A1 | 1/2003 | Thompson et al. | |
| 2004/0073265 A1 | 4/2004 | Scheiner | |
| 2004/0098065 A1 | 5/2004 | Hagglof et al. | |
| 2005/0209654 A1 | 9/2005 | Boveja et al. | |
| 2005/0240229 A1 | 10/2005 | Whitehurst et al. | |
| 2007/0027494 A1 | 2/2007 | Gerber | |
| 2007/0027497 A1 | 2/2007 | Parnis | |
| 2007/0027501 A1 | 2/2007 | Jensen | |
| 2007/0060991 A1 | 3/2007 | North et al. | |
| 2007/0123952 A1 | 5/2007 | Strother et al. | |
| 2007/0213795 A1 | 9/2007 | Bradley et al. | |
| 2008/0071321 A1 | 3/2008 | Boggs et al. | |
| 2008/0132969 A1 | 6/2008 | Bennett et al. | |
| 2008/0154179 A1 | 6/2008 | Cantor et al. | |
| 2008/0161874 A1* | 7/2008 | Bennett ............. | A61N 1/36017 607/39 |
| 2008/0292685 A1 | 11/2008 | Wang et al. | |
| 2009/0054952 A1 | 2/2009 | Glukhovsky et al. | |
| 2009/0149917 A1 | 6/2009 | Whitehurst et al. | |
| 2009/0182216 A1 | 7/2009 | Roushey et al. | |
| 2009/0198306 A1 | 7/2009 | Goetz et al. | |
| 2010/0036445 A1 | 2/2010 | Sakai et al. | |
| 2010/0072334 A1 | 3/2010 | Le Gette et al. | |
| 2010/0106204 A1 | 4/2010 | Moffit et al. | |
| 2010/0198044 A1 | 8/2010 | Gehman et al. | |
| 2010/0274327 A1* | 10/2010 | Carroll ................ | A61N 1/0456 607/148 |
| 2010/0324620 A1 | 12/2010 | Libbus et al. | |
| 2011/0125214 A1 | 5/2011 | Goetz et al. | |
| 2011/0208123 A1 | 8/2011 | Gray et al. | |
| 2011/0270068 A1 | 11/2011 | Mehdizadeh et al. | |
| 2012/0035496 A1* | 2/2012 | Denison ............... | A61B 5/7203 600/547 |
| 2012/0123496 A1 | 5/2012 | Schotzko et al. | |
| 2012/0123502 A1* | 5/2012 | Aghassian ............ | A61N 1/025 607/59 |
| 2016/0296754 A1 | 10/2016 | Kaula et al. | |

OTHER PUBLICATIONS

Patient Trial Handbook: Precision Spinal Cord Stimulation System, Advanced Bionics, Part No. 9055078-001 Rev C, 2003, 36 pages.

Physician Lead Manual: Precision Spinal Cord Stimulation System, Advanced Bionics, Part No. 9055095-001 Rev C, 2003, 51 pages.

Physician Trial Kit Model SC-7005-02, Advanced Bionics, Part No. MP9055214 Rev A, 2004, 2 pages.

Bartels et al., "Long-Term Evaluation of Treatment of Chronic, Therapeutically Refractory Tinnitus by Neurostimulation," Stereotactic and Fungal Neurosurgery, vol. 85, 2007, pp. 150-157.

Taking SCS for a Test Drive, Retrieved online from https://web.archive.org/web/20110806190212/http://controlyourpain.com:80/control/test_drive.cfm, 2011, 2 pages.

Deng et al., "Failure of Sacral Nerve Stimulation Due to Migration of Tined Lead," The Journal of Urology, vol. 175, Jun. 2006, pp. 2182-2185.

Summary of Safety and Effectiveness, Precision Spinal Cord Stimulator (SCS) System, Advanced Bionics, Premarket Approval Application No. P030017, Apr. 27, 2004, 18 pages.

Draft Patient Trial Handbook, Advanced Bionics, Part No. MP9055185 Rev A, 2004, 68 pages.

Holm et al., "Neurostimulation as a New Treatment for Severe Tinnitus: A Pilot Study," Otology & Neurotology, vol. 26, No. 3, 2005, pp. 425-428.

Jandial et al., "Effect of Vagus Nerve Stimulator Magnet on Programmable Shunt Settings," Neurosurgery, vol. 55, No. 3, Sep. 2004, pp. 627-630.

Krames et al., "Spinal Cord Stimulation Has Comparable Efficacy in Common Pain Etiologies," Neuromodulation: Technology at the Neural Interface, vol. 11, No. 3, 2008, pp. 171-181.

Merrill, "Review of electrical stimulation in cerebral palsy and recommendations for future directions," Developmental Medicine & Child Neurology, vol. 51, Supp. 4, 2009, pp. 154-165.

Norderval et al., "Sacral nerve stimulation," Tidsskr Nor Legefoen, No. 12, 2011, pp. 1190-1193.

Oakley et al.," A New Spinal Cord Stimulation System Effectively Relieves Chronic, Intractable Pain: A Multicenter Prospective Clinical Study," Neuromodulation: Technology at the Neural Interface, vol. 10, No. 3, 2007, pp. 262-278.

Oakley et al., "Successful Long-Term Outcomes of Spinal Cord Stimulation Despite Limited Pain Relief During Temporary Trialing," Neuromodulation: Technology at the Neural Interface, vol. 11, No. 1, 2008, pp. 66-73.

Opisso et al., "Patient Controlled Versus Automatic Stimulation of Pudendal Nerve Afferents to Treat Neurogenic Detrusor Overactivity," The Journal of Urology, vol. 180, Oct. 2008, pp. 1403-1408.

(56) References Cited

OTHER PUBLICATIONS

Pereira et al., "Appetite Suppression and Weight Loss Incidental to Spinal Cord Stimulation for Pain Relief," Obesity Surgery, vol. 17, 2007, pp. 1272-1274.
International Patent Application No. PCT/US2013/029273, International Search Report and Written Opinion dated May 26, 2014, 18 pages.
European Patent Application No. 13712403.8, Examination Report dated Feb. 15, 2018, 4 pages.
Prosecution History from U.S. Appl. No. 14/396,659, dated Oct. 23, 2014 through Mar. 25, 2019, 211 pages.
Prosecution History from U.S. Appl. No. 14/396,671, dated Oct. 23, 2014 through Dec. 12, 2017, 249 pages.
Elterman, "The novel Axonics® rechargeable sacral neuromodulation system: Procedural and technical impressions from an initial North American Experience," Neurourology and Urodynamics, Jan. 16, 2018, pp. 1-8.

* cited by examiner

TRIAL STIMULATION SYSTEMS

This application is a continuation of U.S. patent application Ser. No. 16/530,636, filed Aug. 2, 2019, which is a continuation of U.S. patent application Ser. No. 14/396,659, filed Oct. 23, 2014, which is a national stage application under 35 U.S.C. § 371 of International Application No. PCT/US2013/029273 filed on Mar. 6, 2013, which claims the benefit of U.S. Provisional Patent Application Ser. No. 61/638,933, filed Apr. 26, 2012, and entitled "TRIAL STIMULATION SYSTEMS," the entire contents of application Ser. Nos. 16/530,636, 14/396,659, PCT/US2013/029273, and 61/638,933 are incorporated herein by reference.

TECHNICAL FIELD

The disclosure relates to medical devices.

BACKGROUND

A variety of medical devices are used for chronic, e.g., long-term, delivery of therapy to patients suffering from conditions that range from chronic pain, tremor, Parkinson's disease, and epilepsy, to urinary or fecal incontinence, sexual dysfunction, obesity, spasticity, and gastroparesis. As an example, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each parameter in a set of therapeutic parameters specified by a clinician.

Chronic implantation of a stimulation generator and one or more leads for delivering stimulation therapy to a patient may be preceded by a trial period. The trial period ordinarily has a prescribed maximum duration, but sometimes is exceeded by the patient or the physician. During the trial period, a clinician evaluates the efficacy of stimulation in alleviating the patient's disorder to determine whether the patient is a good candidate for chronic implantation. The trial period ordinarily involves implantation of a temporary or chronic lead, and percutaneous connection of the lead to an external trial stimulator. Often, connection of the lead to the trial stimulator involves extensive subcutaneous tunneling of the lead to a percutaneous exit site.

SUMMARY

Examples according to this disclosure are directed to trial electrical stimulation systems for delivering medical therapy. A trial stimulation system may include a disposable trial stimulator that is sterilized for a single use in a stimulation trial of one patient. The following examples also include a device for securing a disposable trial stimulator to the body of a patient, which may function to improve the durability of the system during the trial period and reduce the risk of damage to or malfunction of the system due to lead/electrode dislocation and/or off-label uses like showering or bathing with the trial stimulator still secured to the body.

In one example according to this disclosure, a medical system includes a disposable trial electrical stimulator, at least one percutaneous stimulation lead, and an electronic programming device. The disposable trial stimulator includes a single user interface integral with the trial stimulator. The at least one percutaneous stimulation lead is connected to the trial stimulator. The electronic programming device is configured to wirelessly communicate with the trial stimulator to program the trial stimulator to deliver stimulation therapy via the at least one percutaneous stimulation lead. The user interface is configured to cause the trial stimulator to be capable of wireless communications with the electronic programming device and to turn off stimulation being delivered by the trial stimulator.

In another example, a disposable trial electrical stimulator includes a pulse generator, a lead coupler, and a processor. The pulse generator is configured to deliver electrical stimulation via at least one stimulation lead connected to the trial stimulator. The lead coupler is configured to connect the at least one stimulation lead directly to the trial stimulator without any intervening lead connection devices. The lead coupler is also configured to connect a plurality of types of stimulation leads directly to the trial stimulator without any intervening lead connection devices. The processor is configured to control the pulse generator to deliver the electrical stimulation via the at least one stimulation lead. The trial stimulator is sterilized.

In another example, a system for securing a disposable trial stimulator to a body of a patient includes a patch and a holster. The patch includes a first major surface at least partially covered with an adhesive configured to adhere the patch to the body of the patient. The holster is connected to a second major surface of the patch. The holster is configured to receive the trial stimulator.

In another example, a method includes implanting at least one percutaneous stimulation lead to deliver stimulation to a target tissue location and connecting the at least one percutaneous stimulation lead to a disposable trial stimulator comprising a single user interface integral with the trial stimulator. The user interface is configured to cause the trial stimulator to be capable of wireless communications with the programmer and to turn off stimulation being delivered by the trial stimulator. The method also includes programming the trial stimulator to deliver stimulation via the at least one percutaneous stimulation lead with an electronic programming device configured to wirelessly communicate with the trial stimulator, delivering stimulation to the target tissue location via the at least one percutaneous stimulation lead with the trial stimulator for a trial period of time, and disposing of the trial stimulator after expiration of the trial period of time.

In another example, a method includes implanting a percutaneous stimulation lead to deliver stimulation to a target tissue location and connecting the percutaneous stimulation lead directly to a disposable trial stimulator via a lead coupler integral with the trial stimulator. The lead coupler is configured to connect a plurality of types of percutaneous stimulation leads directly to the trial stimulator without any intervening lead connection devices. The method also includes programming the trial stimulator to deliver stimulation via the percutaneous stimulation lead with an electronic programming device configured to wireless communicate with the trial stimulator, delivering stimulation to the target tissue location via the percutaneous stimulation lead with the trial stimulator for a trial period of time, and disposing of the trial stimulator after expiration of the trial period of time.

In another example, a method of securing a disposable trial stimulator to a body of a patient includes implanting a percutaneous stimulation lead to deliver stimulation to a target tissue location and adhering a first major surface of a patch at least partially covered with an adhesive to the body of the patient. A holster is connected to a second major surface of the patch and the holster is configured to receive the trial stimulator. The method also includes inserting the trial stimulator into the holster and connecting the percutaneous stimulation lead to the trial stimulator.

The details of one or more aspects of the disclosure are set forth in the accompanying drawings and the description below. Other features, objects, and advantages of the examples of the disclosure will be apparent from the description and drawings, and from the claims.

DETAILED DESCRIPTION

Figure 1:
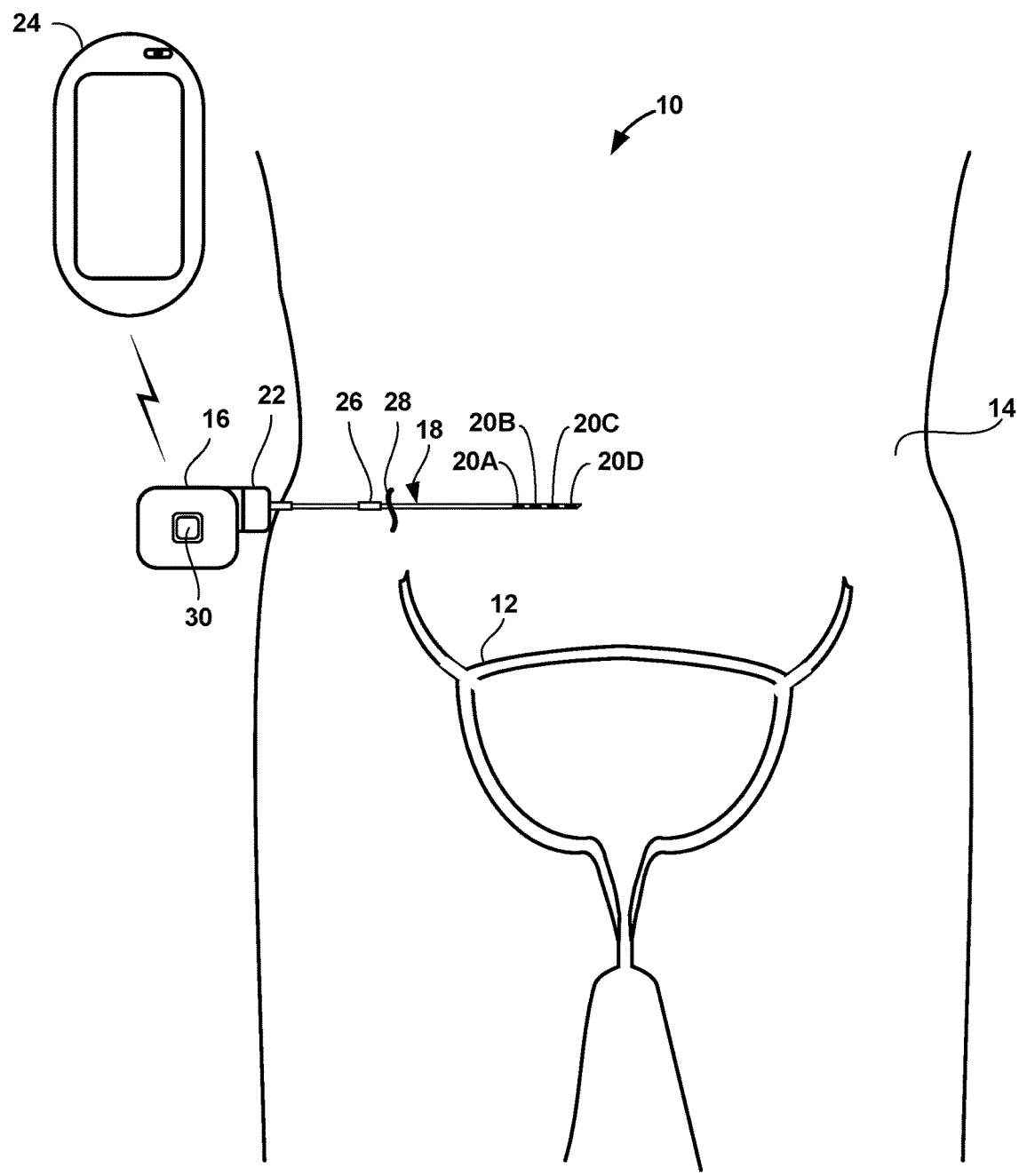
FIG. 1 is a conceptual diagram illustrating an example trial stimulation system according to this disclosure.

This disclosure is directed to electrical stimulation therapy delivered via a trial stimulator during a trial stimulation period. Prior to a decision to implant a chronic neurostimulation device, e.g. a spinal cord stimulation device used to deliver therapy for chronic pain, a deep brain stimulation (DBS) device used to deliver therapy for any of a variety of brain disorders, a gastric stimulation device used to deliver therapy for gastroparesis or gastro-intestinal disorders or obesity, or a pelvic floor stimulation device used to treat urgency and/or urinary incontinence, pelvic pain, sexual dysfunction, or other disorders, patients typically undergo an evaluation phase of 1-3 weeks using an external trial stimulator connected to one or more stimulation leads. Current trial stimulation systems share a number of negative attributes.

Current trial stimulation systems include a reusable trial stimulator. Some such reusable trial stimulators include, not only the electronics and power source necessary to deliver stimulation therapy via one or more leads, but also a number of user input/output (I/O) controls that are necessary for operation of the system. Because current trial stimulators are reusable, such devices generally cannot be sterilized between trials and are therefore kept out of the sterile field during the surgical procedure in which the leads of the trial stimulation system are implanted and initial stimulation testing takes place. Such reusable trial stimulators, which are not designed to be sterilized, are kept out of the sterile field during surgery to prevent cross contamination of blood or other bodily fluids between different trials employing the same stimulator.

It has been generally considered that designing the trial stimulator to be reusable is an advantage, as it may reduce waste and costs. However, the inability to sterilize the device and the requirement that the device be outside of the sterile field during surgery, may lead to several consequences that may outweigh the benefits of reusability. For example, during intraoperative stimulation testing of a trial stimulation system including a reusable non-sterile trial stimulator, a wired connection is required between the sterile components of the system, e.g. leads and the stimulator. This wired connection must cross the sterile field perimeter. The inability to maintain the integrity of the sterile field during surgery may allow potentially harmful microbes to travel into or out of the sterile field, which may, in turn, lead to complications such as contamination and/or infection.

After surgery during the at-home phase of the stimulation trial, current trial systems commonly employ leads, which are connected to a lead extension and/or adaptor connected to a trial stimulator that is worn externally on the clothing or a lanyard. Externalization of the trial stimulator, as well as the necessity for the lead extension and/or adaptor, may increase the likelihood of inaccurate tests results because system wires can become hung up on clothing or the environment (door knob) or otherwise interfered with, potentially causing dislocation of the stimulating electrodes within the body of the patient.

Another disadvantage of current trial stimulation systems is the manner in which users interact with the system to control stimulation therapy or otherwise interact with the trial stimulator. In some current systems, as noted above, the trial stimulator includes a number of user input/output controls that are necessary for operation of the system. However, as the trial stimulator in some such systems is commonly held or secured to the back of the patient, it is inconvenient or impractical for the patient to interact with the I/O devices integral with the stimulator. The inclusion of I/O devices integral with the trial stimulator also prevents maintaining the sterile field during surgery, as it may be necessary to interact with such devices during intraoperative testing of the stimulator. Additionally, some current trial stimulation systems utilize programming devices for modulating the therapy, which, while separate from the trial stimulator, must nevertheless be directly next to or very near the stimulator to communicate with it. Again, due to the placement of the trial stimulator on or near the back of the patient, such programming devices may be inconvenient or impractical to use.

In view of the foregoing challenges, examples according to this disclosure are directed to trial stimulation systems that include a disposable trial stimulator that is sterilized for a single use in a stimulation trial of one patient. The following examples also include a device for securing a disposable trial stimulator to the body of a patient, which may function to improve the durability of the system during the trial period and reduce the risk of damage or malfunction to the system due to lead/electrode dislocation and/or off-label uses like showering or bathing with the trial stimulator still secured to the body.

In one example according to this disclosure, a medical system includes a disposable trial stimulator, at least one percutaneous stimulation lead, and an electronic programming device. The disposable trial stimulator includes a single user interface integral with the trial stimulator. The at least one percutaneous stimulation lead is connected to the trial stimulator. The electronic programming device is configured to wirelessly communicate with the trial stimulator to program the trial stimulator to deliver stimulation therapy via the at least one percutaneous stimulation lead. The user interface may include, e.g., a button, rocker switch, slider switch, or rotary dial switch and is configured to cause the trial stimulator to be capable of wireless communications with the electronic programming device and to turn off stimulation being delivered by the trial stimulator.

Stimulation leads referred to in this disclosure as "percutaneous" leads may include leads that are not fully implanted within the body of a patient and, instead, are arranged partially implanted through an incision in the skin. As such, a percutaneous lead does not necessarily refer to the surgical process by which the lead is partially implanted within the body, e.g., percutaneously or surgically via a laminectomy or laminotomy. For example, a percutaneous lead, as referred to in this disclosure, may be surgically placed via a laminectomy or laminotomy. For example, a paddle lead may be employed in a trial stimulation system that treats chronic pain via spinal cord stimulation, which lead may need to be surgically implanted. Nevertheless, the physical arrangement of such a lead in a trial system may be only partially implanted through an incision in the skin. In this manner, "percutaneous" may refer to the physical arrangement of the lead as partially implanted through the skin of the patient versus the manner in which the lead is initially placed by a physician or other clinician.

In another example, a disposable trial stimulator includes a pulse generator, a lead coupler, and a processor. The pulse generator is configured to deliver electrical stimulation via at least one stimulation lead connected to the trial stimulator. The lead coupler is configured to connect the at least one stimulation lead directly to the trial stimulator without any intervening lead connection devices. The lead coupler is also configured to connect a plurality of types of stimulation leads directly to the trial stimulator without any intervening lead connection devices. The processor is configured to control the pulse generator to deliver the electrical stimulation via the at least one stimulation lead. The trial stimulator is sterilized.

In another example, a system for securing a disposable trial stimulator to a body of a patient includes a patch and a holster. The patch includes a first major surface at least partially covered with an adhesive configured to adhere the patch to the body of the patient. The holster is connected to a second major surface of the patch. The holster is configured to receive the trial stimulator.

FIG. 1 is a conceptual diagram illustrating an example therapy system 10 that delivers electrical stimulation therapy to a patient 14. In the example of FIG. 1, for illustration, system 10 is configured to manage an urgency and/or urinary incontinence disorder of patient 14. Urgency and urinary incontinence (e.g., an inability to control urinary function) are problems that afflict people of all ages, genders, and races. Various muscles, nerves, organs and conduits within the pelvic floor cooperate to collect, store and release urine. A variety of disorders may compromise urinary tract performance, and contribute to urgency or incontinence. Many of the disorders may be associated with aging, injury, or illness.

Urgency may originate from disorders of portions of the peripheral or central nervous system which control the bladder micturition reflex. Nerve disorders may also lead to overactive bladder activities and/or may prevent proper triggering and operation of the bladder. Furthermore, urgency or urinary incontinence may also result from improper communication between the nervous system and the urethra. In other examples according to this disclosure, an example trial stimulation therapy system may be configured to treat other conditions, including, e.g., fecal incontinence.

In FIG. 1, therapy system 10 includes an example trial stimulator 16, which is coupled to percutaneous lead 18 including electrodes 20A-20D via lead extension 22. Trial stimulator 16 is also configured to wirelessly communicate with external programmer 24. Trial stimulator 16 generally operates as a trial therapy device that delivers electrical stimulation to, for example, a tissue site proximate a pelvic floor nerve, a pelvic floor muscle, the urinary sphincter, or other pelvic floor targets. Pelvic floor nerves include peripheral nerves such as sacral nerves, pudendal nerves and associated branches, and dorsal genital nerves. In some examples, trial stimulator 16 delivers the electrical stimulation therapy to a sacral nerve of patient 14 to generate an afferent response that relaxes bladder 12, e.g., to reduce a frequency of bladder contractions.

Trial stimulator 16 may be employed by a physician or other clinician to test the efficacy of stimulation therapy for treating a particular patient's condition and also to determine parameters or sets of parameters according to which efficacious stimulation therapy may be delivered to the patient. Trial stimulator 16 may be employed to test stimulation for a patient for a limited, trial period of time, e.g. a number of days, a week or more, or longer than a few weeks. After the trial stimulation period is completed, depending on the results of the trial, trial stimulator 16 and percutaneous lead 18 may be removed and an implantable medical device (IMD) along with one or more implantable leads may be implanted in the patient to deliver chronic stimulation therapy over an extended period of time, e.g. over the operating life of the IMD.

Trial stimulator 16 provides electrical stimulation therapy to patient 14 by generating and delivering electrical stimulation signals to a target therapy site by lead 18 and, more particularly, via electrodes 20A-20D (collectively referred to as "electrodes 20") disposed proximate to a distal end of lead 18. For example, trial stimulator 16 may deliver low intensity stimulation (e.g., subthreshold stimulation) and high intensity electrical stimulation therapies to patient 14 to elicit delayed and immediate physiological responses, respectively. Trial stimulator 16 may also deliver stimulation at intensities between the low intensity and high intensity stimulation. For example, trial stimulator 16 may gradually transition delivery of stimulation from the low intensity to the high intensity in increments defined by, for example, a ramp function, a step function, or a curvilinear function. In some examples, trial stimulator 16 may modify stimulation therapy intensity and duration based on sensor data and/or patient input. As one example, trial stimulator 16 may detect an increased rate of bladder contraction based on sensor data and then modify stimulation (e.g., increase intensity) based on the detected increase in bladder contraction frequency.

Trial stimulator 16 may deliver stimulation therapy to patient 14 according to one or more stimulation parameters, which may be included in stimulation programs and/or program groups. The therapy parameters for a therapy program that controls delivery of stimulation therapy by trial stimulator 16 through the electrodes of lead 18 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms.

As described in more detail with reference to FIGS. 2A-2C, trial stimulator 16 may be configured as a body-worn device that may, in one example, be secured to the back of patient 14. Trial stimulator 16 may be secured to patient 14 in a number of ways, including by, e.g. adhering a surface of the device to the skin of patient 14, e.g., with an adhesive or taping the device to the patient with an adhesive tape. Additionally, FIGS. 8A-9C illustrate systems according to this disclosure for securing body-worn trial stimulators, including, e.g. trial stimulator 16, to the body of a patient.

Trial stimulator 16 has an outer housing that is constructed of a biocompatible material that resists corrosion and degradation from bodily fluids including, e.g., a polymeric material including silicone, polyurethane, or other biologically inert polymers. In one example, the housing of trial stimulator 16 is fabricated from one or more thermoplastics. For example, the housing of stimulator 16 may be fabricated from a polycarbonate and ABS polymer blend. In one example, the housing of trial stimulator 16 may be fabricated from Cycoloy® C2950HF PC+ABS from SABIC Innovative Plastics of Pittsfield Mass. The proximal end of lead 18 is both electrically and mechanically coupled to trial stimulator 16 via lead extension 24. Lead extension includes lead adaptor 26, which may be configured to connect a number of different types of leads to trial stimulator 16. Lead adaptors included in lead extension 24 may vary from the example illustrated in FIG. 1. For example, lead extension 24 may include a lead adapter that is branched such that it is configured to couple multiple percutaneous leads to lead extension 24. Electrical conductors disposed within the lead body of lead 18 electrically connect electrodes 20 to a therapy delivery module (e.g., a stimulation generator) within trial stimulator 16. Although not shown in the example of FIG. 1, trial stimulator 16 may be coupled to additional percutaneous leads. In one example, trial stimulator 16 may be coupled to one or more leads including a number of electrodes for sensing physiological parameters related to delivering urgency and/or urinary incontinence therapy to patient 14. For example, trial stimulator 16 may be coupled to one or more percutaneous leads including electrodes positioned within the body of patient 14 for sensing an impedance of bladder 12, which may decrease as the volume of urine within bladder 12 increases.

Lead 18, and, if provided, other leads coupled to trial stimulator 16, may be percutaneously tunneled through incision 28 to place one or more electrodes, e.g. electrodes 20 carried by a distal end of lead 18 at a desired pelvic nerve or muscle site, e.g., one of the previously listed target therapy sites such as a sacral or pudendal nerve. Electrodes 20 of the common lead 18 may deliver stimulation to the same or different nerves. In other examples of therapy system 10, trial stimulator 16 may be coupled to more than one lead that includes electrodes for delivery of electrical stimulation to different stimulation sites within patient 14, e.g., to target different nerves. In the example shown in FIG. 1, percutaneous lead 18 is cylindrical. Electrodes 20 may be cuff electrodes, ring electrodes, segmented electrodes or partial ring electrodes. In one example, lead 18 may include a paddle-shaped distal end on which one or more electrodes are arranged.

Trial stimulator 16 may include one or more sensors for detecting changes in the contraction of bladder 12 as a mechanism for improving the efficacy of therapy delivered to patient 14. For example, trial stimulator 16 may include or be coupled to a pressure sensor for detecting changes in bladder pressure, electrodes for sensing pudendal or sacral afferent nerve signals, or electrodes for sensing urinary sphincter EMG signals, or any combination thereof. In other examples, trial stimulator 16 may include a patient motion sensor that generates a signal indicative of patient activity level or posture state. In some examples, trial stimulator 16 controls the delivery of stimulation therapy to patient 14 based on sensed patient activity level or posture state. For example, a patient activity level that is greater than or equal to a threshold may indicate that there is an increase in urgency and/or an increase in the probability that an incontinence event will occur, and accordingly, trial stimulator 16 may provide electrical stimulation based on the patient activity level. As an additional example, patient 14 may be more prone to urgency or an incontinence event when patient 14 is in an upright posture state compared to a lying down posture state. Accordingly, in some examples, trial stimulator 16 may control the delivery of electrical stimulation to patient based on the patient posture state determined based on a signal generated by a motion sensor.

System 10 includes an external programmer 24, as shown in FIG. 1. In some examples, programmer 24 may be a wearable communication device, handheld computing device, computer workstation, or networked computing device. Programmer 24 may include a user interface that receives input from a user (e.g., patient 14, a patient caretaker or a clinician). The user interface may include a keypad and a display (e.g., an LCD display). The keypad may take the form of an alphanumeric keypad or a reduced set of keys associated with particular functions of programmer 24. Programmer 24 can additionally or alternatively include a peripheral pointing device, such as a mouse, via which a user may interact with the user interface. In some examples, a display of programmer 24 may include a touch screen display, and a user may interact with programmer 24 via the touch screen display. It should be noted that the user may also interact with programmer 24 and/or trial stimulator 16 remotely via a networked computing device.

Patient 14 may interact with programmer 24 to control trial stimulator 16 to deliver the stimulation therapy, to manually abort the delivery of the stimulation therapy by trial stimulator 16 while trial stimulator 16 is delivering the therapy or is about to deliver the therapy, or to inhibit the delivery of the stimulation therapy by trial stimulator 16, e.g., during voluntary voiding events. Patient 14 may, for example, use a touch screen of programmer 24 to cause trial stimulator 16 to deliver the stimulation therapy, such as when patient 14 senses that a leaking episode may be imminent. In this way, patient 14 may use programmer 24 to control the delivery of the stimulation therapy "on demand," e.g., when extra stimulation therapy is desirable.

Patient 14 may interact with programmer 24 to inhibit the delivery of the stimulation therapy during voluntary voiding events or to modify the type of stimulation therapy that is delivered (e.g., to control trial stimulator 16 to deliver stimulation therapy to help patient 14 voluntarily void in examples in which patient 14 has a urinary retention disorder). That is, patient 14 may use programmer 24 to enter input that indicates the patient will be voiding voluntarily.

When trial stimulator 16 receives the input from programmer 24, trial stimulator 16 may suspend delivery the stimulation therapy for a predetermined period of time, e.g., two minutes, to allow the patient to voluntarily void, or switch to a different type of stimulation therapy to help patient 14 voluntarily void.

A user other than patient 14, such as a physician, technician, surgeon, electrophysiologist, or other clinician, may also interact with programmer 24 or another separate programmer (not shown), such as a clinician programmer to communicate with trial stimulator 16. Such a user may interact with a programmer to retrieve physiological or diagnostic information from trial stimulator 16. The user may also interact with a programmer to program trial stimulator 16, e.g., select values for the stimulation parameters according to which trial stimulator 16 generates and delivers electrical stimulation and/or other operational parameters of trial stimulator 16. For example, the user may use programmer 24 to retrieve information from trial stimulator 16 regarding the contraction of bladder 12 and voiding events. As another example, the user may use programmer 24 to retrieve information from trial stimulator 16 regarding the performance or integrity of trial stimulator 16 or other components of system 10, such as lead 18, or a power source of trial stimulator 16.

Trial stimulator 16 and programmer 24 communicate wirelessly. Examples of wireless communication techniques employed by stimulator 16 and programmer 24 may include, for example, low frequency or radiofrequency (RF) telemetry, but other techniques are also contemplated.

Trial stimulator 16 may commonly be secured to the body of patient 14 in a position that makes manipulation of controls integral with the stimulator inconvenient or impractical. For example, trial stimulator 16 may be secured to the back of patient 14 adjacent the waste line of the patient. As such, the vast majority of interaction with and control of trial stimulator 16 is executed by users via electronic programmer 24, which wireless communicates with the stimulator. Trial stimulator 16 does include, however, a single user interface, button 30 integral with the stimulator. Button 30 is conveniently located on one of the two larger faces of trial stimulator 16, e.g. in the center of the face as illustrated in FIG. 1, to make the control easier for patient 14 to locate. Additionally, button 30 may include structural features to make it easier to locate, like a raised edge around the perimeter of the button or a surface finish or coating or texture that differs from the other surfaces of trial stimulator 16. Button 30 is employed for two important functions that may not be best executed by programmer 24. In particular, button 30 is configured to cause trial stimulator 16 to be capable of wireless communication with programmer 24 and to turn off stimulation being delivered by the trial stimulator, e.g., in the event that patient 14 wishes to cease stimulation quickly without accessing a feature-rich user interface via programmer 24 or because programmer 24 is unavailable. In other examples according to this disclosure, a trial stimulator may include a single user interface integral with the stimulator that is different than a button, e.g. a rocker switch, slider switch, or rotary dial switch.

Figure 2A:
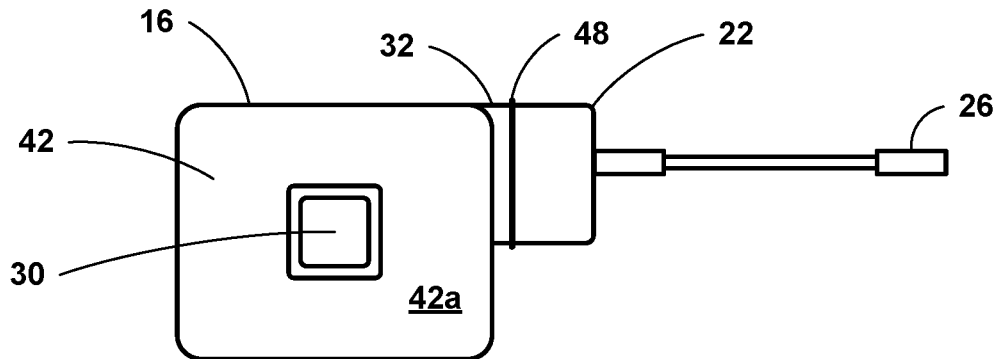
FIGS. 2A-2C are conceptual diagrams of a number of views of the example trial stimulator of the system of FIG. 1.
Figure 2B:
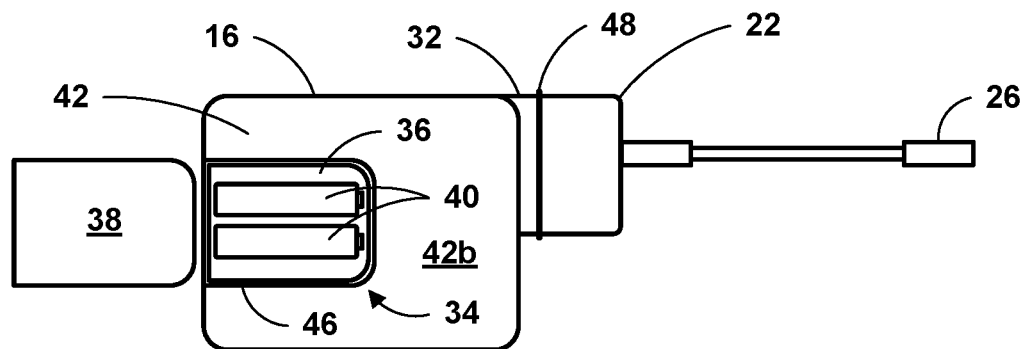
Figure 2C:
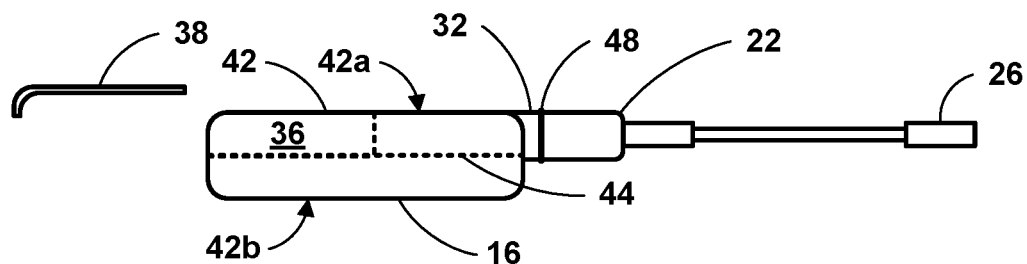

FIGS. 2A-2C are conceptual diagrams of a number of views of example trial stimulator 16 of trial system 10 of FIG. 1. In FIGS. 2A-2C, trial stimulator 16 includes button 30 and is connected to lead extension 22 via coupler 32. In one example, lead extension 22 may include a male electrical connector, or plug that is configured to be received in a female electrical connector, or, socket of coupler 32 of trial stimulator 16. In another example, lead extension 22 may include a female electrical connector, or, socket that is configured to be received in a male electrical connector, or, plug of coupler 32 of trial stimulator 16. Trial stimulator 16 also includes battery bay 34, which includes cavity 36 and door 38. Battery bay 34 is configured to receive one or more rechargeable or primary source batteries configured to power trial stimulator 16. In one example, as illustrated in FIG. 2B, battery bay 34 is configured to receive a plurality of batteries, e.g., two AAAA dry cell alkaline batteries 40.

Trial stimulator 16 is configured to be disposed of after a single trial with one patient, e.g. patient 14. As such, trial stimulator 16 may be sterilized prior to use in a trial and may be arranged within a sterile field during surgery and intraoperative testing of the stimulator. Because trial stimulator 16 is within the sterile field during surgery, the stimulator may encounter blood and other bodily fluids. Additionally, there may be instances in which trial stimulator 16 is subject to off-label uses by a patient, including showering or bathing with the device. As such, in one example, trial stimulator 16 is configured to resist ingress of liquid into the device.

In some examples, trial stimulator 16 may not be hermetically sealed, as structures and processes for achieving a hermetic seal may present too great a cost for a disposable device like disposable trial stimulator 16. Trial stimulator 16 may, however, employ a number of techniques to resist ingress of liquid into the device. In one example, housing 42 of trial stimulator 16 is configured to resist ingress of liquid into an interior chamber defined by the housing. As illustrated in FIG. 2C, housing 42 may be include a first, or top half 42a, and a second, or bottom half 42b, which are joined at seam 44. Top half 42a and bottom half 42b may be joined at seam 44 by an ultrasonic weld that is configured to seal an interior chamber defined by housing 42 when top and bottom halves 42a, 42b are joined. Additionally, trial stimulator 16 may include a seal that resists ingress of liquids into the device at the interface between battery bay door 38 and bottom half 42b of housing 42. For example, as illustrated in FIG. 2B, gasket 46 may be interposed between battery bay door 38 and housing 42 to resist ingress of fluids into battery bay 34. Additionally, the junction between lead extension 22 and trial stimulator 16 via coupler 32 may be sealed with gasket 48, which, in one example, may take the form of an O-ring. Gasket 48 between lead extension 22 and coupler 32 may be configured to resist ingress of liquids into contact with the electrical connection between extension 22 and coupler 32.

Example disposable trial stimulator 16 of FIGS. 1 and 2A-2C may include a number of additional features. In one example, trial stimulator 16 may be configured to automatically, and without user interaction, detect the type of percutaneous stimulation lead 18 connected to the trial stimulator via lead extension 22. In one example, lead adaptor 26 may include, in addition to electrical connections for connecting lead 18 to stimulator 16, an electrical contact that is configured to connect with a conductor of stimulation lead 18 in order to close a circuit that is configured to facilitate autonomous detection of the type of lead 18 connected to stimulator 16. For example, adaptor 26 may include an electrical contact that connects a conductor of stimulation lead 18 to a controlled current source included in stimulator 16 that is configured to deliver a particular amount of current across the lead conductor. The circuit with the controlled current source included in trial stimulator 16 may be configured to measure the voltage drop across the lead conductor. Trial stimulator 16, e.g. a processor of trial stimulator 16 may then calculate the resistance of the conductor of lead 18 based on the delivered current and the measured voltage. In any event, Trial stimulator 16 may compare the actual resistance of the conductor of stimulation lead 18 to a plurality of resistances associated with a plurality of lead types, e.g. stored in memory of trial stimulator 16 and/or programmer 24.

In one example, trial stimulator 16 may not calculate resistance in order to detect the type of lead connected thereto. Instead, the circuit with the controlled current source included in trial stimulator 16 may be configured to measure the voltage drop across the lead conductor and trial stimulator 16 may compare the measured voltage drop across the lead conductor to stored voltage values associated with different lead types. Trial stimulator 16 may then determine the lead type based on the comparison between measured voltage and stored voltage.

Autonomous lead detection may improve the efficiency and control of programming stimulation therapy delivery for trial stimulator 16. For example, trial stimulator 16 may be configured to automatically limit at least one of a number of stimulation programming options available via programmer 24, limit or select one or more stimulation parameter values, or select different programs according to which the trial stimulator can deliver stimulation via stimulation lead 18 based on the type of the lead detected by the device.

In one example, trial stimulator 16 includes a diagnostics module configured to automatically cease delivery of stimulation when stimulation lead 18 is disconnected from the trial stimulator, either by lead extension 22 being disconnected from coupler 22 or by lead 18 being disconnected from lead extension 22. Additionally, the diagnostics module of trial stimulator 16 may be configured to monitor stimulation intensity delivered by trial stimulator 16 via lead 18 and generate an alert when the stimulation intensity delivered by trial stimulator 16 does not equal a programmed stimulation intensity, e.g. stored in memory of stimulator 16 and/or programmer 24.

For example, stimulation lead 18 may include additional conductors that function as resistors at the connection with trial stimulator 16 via lead extension 22. Trial stimulator 16 may then be configured to detect the presence or absence of this resistor, e.g., by delivering current across the resistor from a power source of the stimulator. In the event, the resistance of the additional conductor is not detected, trial stimulator 16 may, e.g., automatically turn off stimulation and log an error in memory of the device. Trial stimulator 16 may also generate a visual, audible, or tactile alert or communicate with programmer 24 to cause the programmer to generate an alert.

With regard to monitoring stimulation intensity, a stimulation engine of trial stimulator 16 may be configured to measure the actual output energy of stimulation delivered by stimulator 16. In the event the actual stimulation output does not equal the programmed stimulation, an error may be generated and logged and, in some examples, trial stimulator 16 may generate an alert. Depending on the nature of the stimulation error, e.g., the magnitude of the discrepancy between programmed stimulation intensity and actual output, a diagnostic module of trial stimulator 16 may prevent stimulation. In another example, trial stimulator 16 may detect is if the impedance in stimulation lead 18 is either too low or too high and, e.g., trigger an alert as appropriate.

Figure 3:
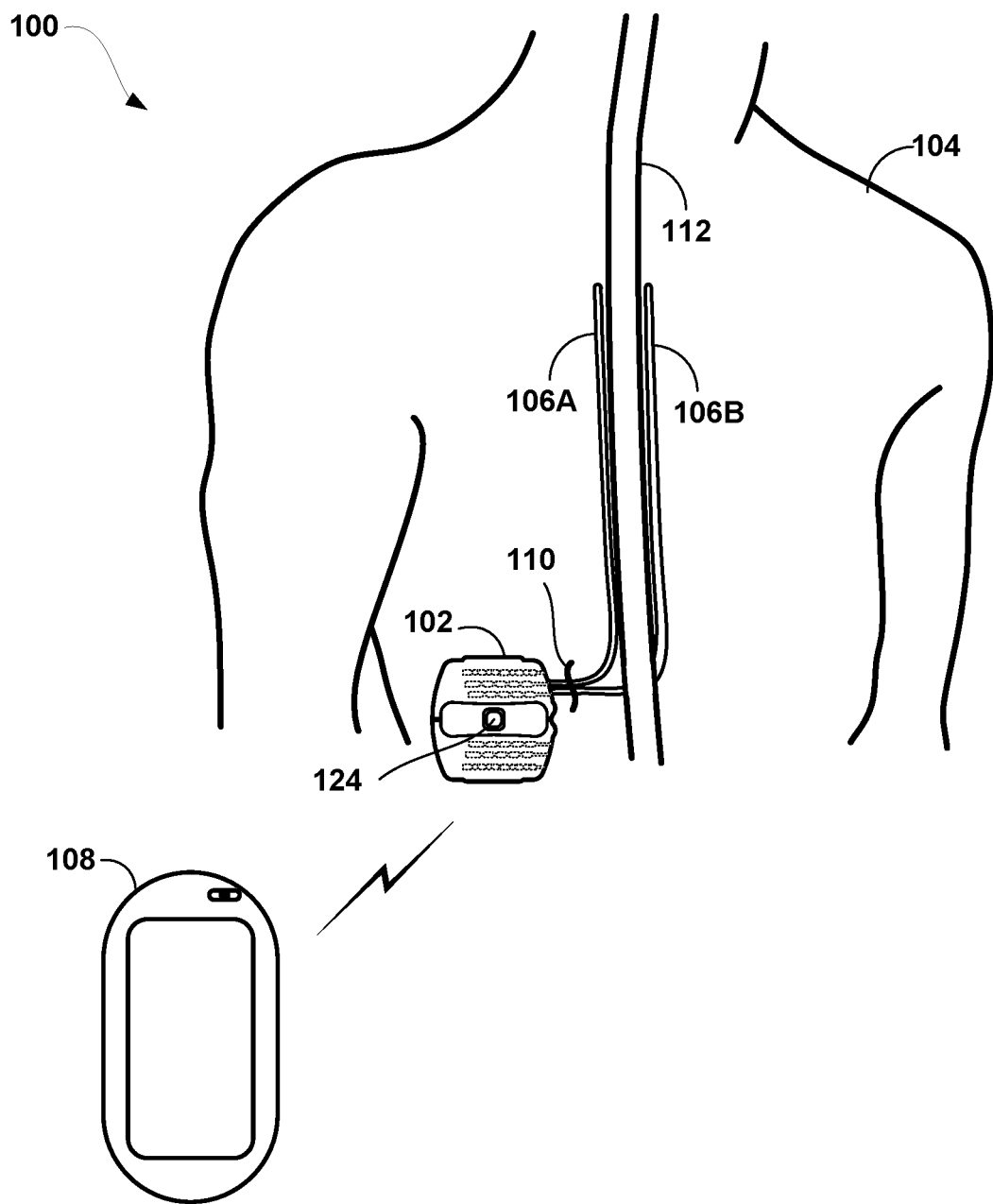
FIG. 3 is a conceptual diagram illustrating another example trial stimulation system according to this disclosure.

FIG. 3 is a schematic diagram illustrating another example trial stimulation system 100 including trial stimulator 102 coupled to a pair of percutaneous electrode arrays in the form of stimulation leads 106A and 106B. Example trial stimulation system 100 including trial stimulator 102 is configured to be employed in a spinal cord stimulation (SCS) trial. The components of trial stimulation system 102 may generally include similar structures, functions, and variety of options described above with reference to trial stimulation system 10 of FIG. 1. For example, the construction and general function of trial stimulator 102 to deliver electrical stimulation via leads 106A and 106B to the spinal cord of patient 104 may be similar to that described above with reference to trial stimulator 16 and lead 18, including the construction and optional types of leads employed, the materials from which the housing of stimulator 102 is constructed, communications between programmer 108 and stimulator 102 and other general features and functions of trial stimulation system 100. Differences between system 10 of FIG. 1 and system 100 will be apparent from the following description of the components of and therapy delivered by trial stimulation system 100.

As shown in FIG. 3, system 100 includes disposable trial stimulator 102, stimulation leads 106A and 106B, and external programmer 108, all of which are shown in conjunction with patient 104. In the example of FIG. 3, trial stimulator 102 is a disposable electrical stimulator configured for SCS, e.g., for relief of chronic pain or other symptoms. Stimulation leads 106A and 106B are connected to trial stimulator 102 and implanted through incision 110 and then tunneled through tissue of patient 104 to a therapy delivery site proximate spinal cord 112. Patient 104 is ordinarily a human patient, but may also be a non-human patient including, e.g., a primate, canine, equine, pig, and feline.

Trial stimulator 102, in general, has an outer housing that is constructed of a biocompatible material that resists corrosion and degradation from bodily fluids including, e.g., a polymeric material including silicone, polyurethane, or other biologically inert polymers. In one example, the housing of trial stimulator 102 is fabricated from one or more thermoplastics. For example, the housing of stimulator 102 may be fabricated from a polycarbonate and ABS polymer blend. In one example, the housing of trial stimulator 102 may be fabricated from Cycoloy® C2950HF PC+ABS from SABIC Innovative Plastics of Pittsfield, Mass. As described in more detail with reference to FIGS. 4A and 4B, trial stimulator 102 is a body-worn device that may, in one example, be secured to the back of patient 104. Trial stimulator 102 may be secured to patient 104 in a number of ways, including by, e.g. adhering a surface of the device to the skin of patient 104 with an adhesive or taping the device to the patient with an adhesive tape. Additionally, FIGS. 8A-9C illustrate systems according to this disclosure for securing body-worn trial stimulators, including, e.g. trial stimulator 102, to the body of a patient.

Stimulation energy is delivered from trial stimulator 102 to spinal cord 112 of patient 104 via one or more electrodes of implantable leads 106A and 106B (collectively "leads 106"). The electrodes (not shown) may be, e.g., electrode pads on a paddle lead, circular (e.g., ring) electrodes surrounding the body of leads 106, conformable electrodes, cuff electrodes, segmented electrodes, or any other type of electrodes capable of forming unipolar, bipolar or multipolar electrode configurations for therapy. In some applications, such as SCS to treat chronic pain, the adjacent implantable leads 106 may have longitudinal axes that are substantially parallel to one another.

The therapy parameters for a therapy program that controls delivery of stimulation therapy by trial stimulator 102 through the electrodes of leads 106 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms.

In the example of FIG. 3, leads 106 carry electrodes that are placed adjacent to the target tissue of spinal cord 112. One or more of the electrodes may be disposed at or near a distal tip of a lead 106 and/or at other positions at intermediate points along the lead. As noted above, leads 106 may be implanted percutaneously, or surgically through a laminectomy or laminotomy through incision 110 and coupled to trial stimulator 102.

Trial stimulator 102 delivers electrical stimulation therapy to patient 104 via selected combinations of electrodes carried by one or both of leads 106. The target tissue for the electrical stimulation therapy may be any tissue affected by electrical stimulation energy, which may be in the form of electrical stimulation pulses or continuous waveforms. In some examples, the target tissue includes nerves, smooth muscle or skeletal muscle. In the example illustrated by FIG. 3, the target tissue is tissue proximate spinal cord 112, such as within an intrathecal space or epidural space of spinal cord 112, or, in some examples, adjacent nerves that branch off of spinal cord 112. Leads 106 may be introduced into spinal cord 112 via any suitable region, such as the thoracic, cervical or lumbar regions. Stimulation of spinal cord 112 may, for example, prevent pain signals from traveling through spinal cord 112 and to the brain of patient 104. Patient 104 may perceive the interruption of pain signals as a reduction in pain and, therefore, efficacious therapy results.

In the example of FIG. 3, stimulation energy is delivered by trial stimulator 102, e.g. by a therapy delivery module of trial stimulator 102 to the spinal cord 112 to reduce the amount of pain perceived by patient 104. Although FIG. 3 is directed to SCS therapy, trial stimulation system 100 may alternatively be directed to any other condition that may benefit from stimulation therapy. For example, system 100 may be used to treat urinary urgency or incontinence via sacral stimulation, tremor, Parkinson's disease, epilepsy, sexual dysfunction, obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), gastric stimulation, or any other stimulation therapy capable of treating a condition of patient 104. The electrical stimulation delivered by trial stimulator 102 may take the form of electrical stimulation pulses or continuous stimulation waveforms, and may be characterized by controlled voltage levels or controlled current levels, as well as pulse width and pulse rate in the case of stimulation pulses.

As with trial stimulator 16 of system 10 of FIG. 1, disposable trial stimulator 102 may, in some examples, include one or more sensors configured to monitor or detect a variety of parameters that may be employed in the delivery of stimulation to patient 104, e.g. that may be employed as a basis for improving the efficacy of therapy by modifying stimulation parameters. For example, trial stimulator 102 may include one or more posture sensors configured to detect the posture state and/or activity level of patient 104. During use of trial stimulator 102 to treat patient 104, movement of patient 104 among different posture states may affect the ability of trial stimulator 102 to deliver consistent efficacious therapy. For example, leads 106 may migrate toward trial stimulator 102 when patient 104 bends over, resulting in displacement of electrodes and possible disruption in delivery of effective therapy. Stimulation energy transferred to target tissue may be reduced due to electrode migration, causing reduced efficacy in terms of relief of symptoms such as pain. In such a case, trial stimulator 102 may be configured to automatically modify stimulation parameters based sensor signals indicating patient 104 is bending over. As another example, leads 106 may be compressed towards spinal cord 112 when patient 104 lies down. Such compression may cause an increase in the amount of stimulation energy transferred to target tissue. In this case, the amplitude of stimulation therapy may need to be decreased to avoid causing patient 104 additional pain or unusual sensations, which may be considered undesirable side effects that undermine overall efficacy.

System 100 includes an external programmer 108, as shown in FIG. 3. In some examples, programmer 108 may be a wearable communication device, handheld computing device, computer workstation, or networked computing device. Programmer 108 may include a user interface that receives input from a user (e.g., patient 104, a patient caretaker or a clinician). The user interface may include a keypad and a display (e.g., an LCD display). The keypad may take the form of an alphanumeric keypad or a reduced set of keys associated with particular functions of programmer 108. Programmer 108 can additionally or alternatively include a peripheral pointing device, such as a mouse, via which a user may interact with the user interface. In some examples, a display of programmer 108 may include a touch screen display, and a user may interact with programmer 108 via the touch screen display. It should be noted that the user may also interact with programmer 108 and/or trial stimulator 102 remotely via a networked computing device.

Programmer 108 may function and be used by different users, e.g. patient 104 and a clinician, in a manner similar to that described above with reference to programmer 24 of trial stimulation system 10. Trial stimulator 102 and programmer 108 communicate wirelessly. Examples of wireless communication techniques employed by stimulator 102 and programmer 108 may include, for example, low frequency or radiofrequency (RF) telemetry, but other techniques are also contemplated.

As described above, some current trial stimulation systems commonly employ leads, which are connected to a lead extension and/or adaptor connected to a trial stimulator that is worn externally on the clothing or a lanyard. Externalization of the trial stimulator, as well as the necessity for the lead extension and/or adaptor may increase the likelihood of inaccurate tests results because system wires can become hung up on clothing or the environment (door knob) or otherwise interfered with, potentially causing dislocation of the stimulating electrodes within the body of the patient. Additionally, the use of additional components such as bulky lead extensions and/or adaptors may be costly and inconvenient for patients. Additionally, lead extensions introduce another possible point of failure or malfunction in the connection between lead and stimulator. In view of the foregoing disadvantages of the use of lead extensions and/or adaptors in trial stimulation systems, disposable trial stimulator 102 includes a lead coupler integral with stimulator 102 that connects leads 106 directly to 102 without any intervening lead connection devices.

Figure 4A:
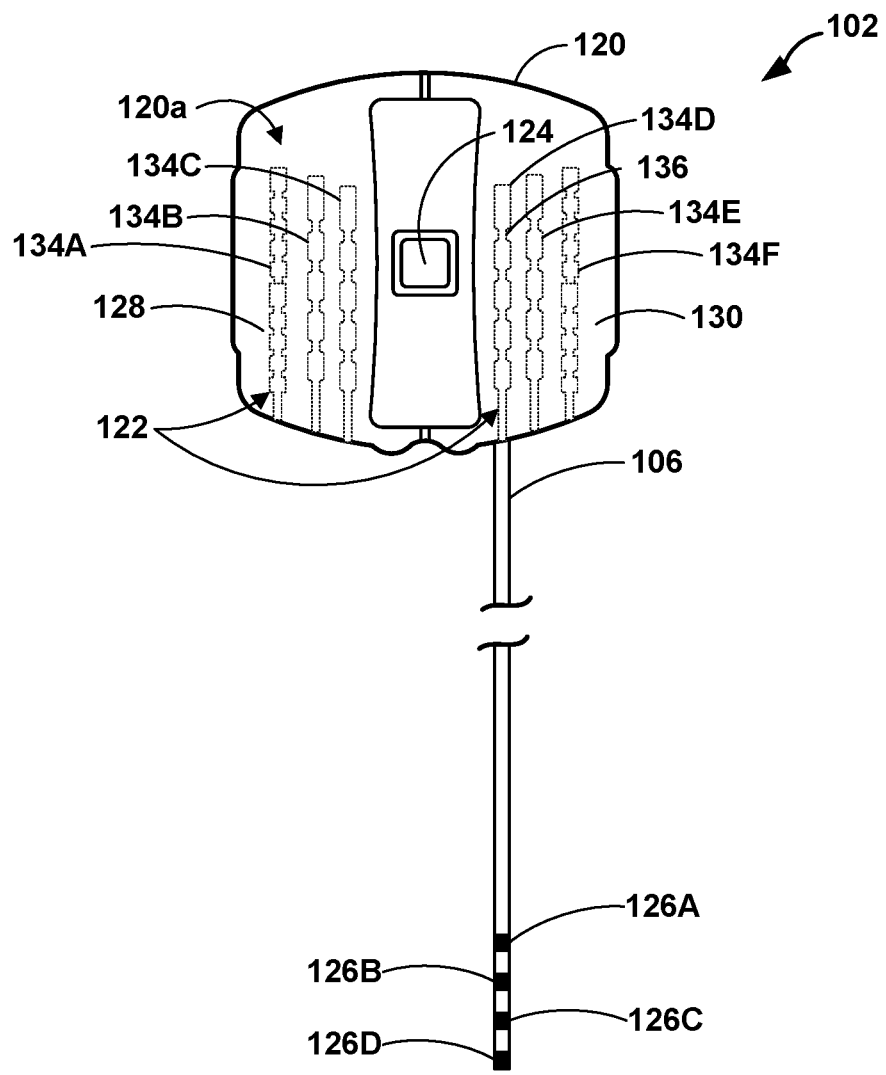
FIGS. 4A and 4B are conceptual diagrams of a number of views of the example trial stimulator of the system of FIG. 3.
Figure 4B:
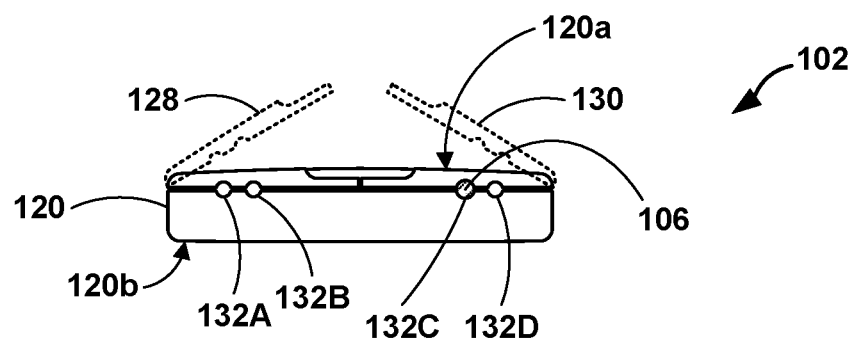

FIGS. 4A and 4B are conceptual diagrams of a number of views of example disposable trial stimulator 102 of system 100 of FIG. 3. In FIGS. 4A and 4B, trial stimulator 102 includes housing 120, lead coupler 122, and button 124. Trial stimulator 102 is connected to lead 106 including four electrodes 126A-126D (collectively "electrodes 126") via lead coupler 122. Housing 120 includes a first, or top half 120*a*, and a second, or bottom half 120*b*. Top half 120*a* of housing 120 includes two lead coupler doors 128 and 130, which are configured to pivot open to expose lead coupler 122. The junction between housing 120 and doors 128 and 130 also includes apertures 132A-132D, which are configured to accommodate, in the example of FIGS. 4A and 4B, up to four percutaneous leads connected to trial stimulator 102 via lead coupler 122.

As noted above and as illustrated in FIG. 4B, lead coupler doors 128 and 130 pivot open to expose lead coupler 122, which in the example of trial stimulator 102 is configured to connect up to four stimulation leads to the disposable stimulator. In other examples, trial stimulator 102 or another disposable trial stimulator according to this disclosure may include a lead coupler configured to accommodate more or fewer stimulation leads than example coupler 122. Opening doors 128 and 130 exposes six slots 134A-134D (collectively "slots 134") included in lead coupler 122. In one example, slots 134 include 2 slots, 134A and 134F with 8 contacts, each of which is configured to receive one lead with eight electrodes. Additionally, slots 134 may include slots 134B-134E with four contacts, each of which is configured to receive one lead with four electrodes, like lead 106 including electrodes 126. Each of slots 134 of lead coupler 122 of trial stimulator 102 is configured to connect one stimulation lead to stimulator 102. For example, percutaneous stimulation lead 106 is connected directly to trial stimulator without any intervening lead connection devices via slot 134D of lead coupler 122. Each of slots 134 may include one or more electrical contacts, like contact 136 illustrated with reference to slot 134D in FIG. 4A. Stimulation leads, like lead 106 may be press fit into slots 134 and may be configured with exposed electrical conductors arranged along the end of the lead received by the slots, e.g. the proximal end of the lead, such that the lead conductors contact the electrical contacts in slots 134. Stimulation leads, like lead 106 may thus be electrically connected to trial stimulator 102 such that stimulator 102 may deliver stimulation therapy to a patient via electrodes arranged at the distal end of the lead, e.g. electrodes 126A-126D and connected to the lead conductors contacting the electrical contacts of slots 134.

In some examples, additional electrical connections between a stimulation lead and lead coupler 122 of trial stimulator 102 may be provided for reasons other than connecting stimulation electrodes to a therapy delivery module of stimulator 102. In one example, each of slots 134 of lead coupler 122 may include an electrical contact that is configured to connect with a conductor of a stimulation lead in order to close a circuit that is configured to facilitate autonomous detection of the type of lead connected to stimulator 102. For example, each of slots 134 of lead coupler 122 may include an electrical contact that connects a conductor of a stimulation lead to a controlled current source that is configured to deliver a particular amount of current across the lead conductor. The circuit with the controlled current source included in trial stimulator 102 may be configured to measure the voltage drop across the lead conductor. Trial stimulator 102, e.g. a processor of trial stimulator may then calculate the resistance of the conductor of the lead based on the delivered current and the voltage. Trial stimulator 102 may compare the actual resistance of the conductor of the stimulation lead to a plurality of resistances associated with a plurality of lead types, e.g. stored in memory of trial stimulator 102 and/or programmer 108.

In one example, trial stimulator 102 may not calculate resistance in order to detect the type of lead connected thereto. Instead, the circuit with the controlled current source included in trial stimulator 102 may be configured to measure the voltage drop across the lead conductor and trial stimulator 102 may compare the measured voltage drop across the lead conductor to stored voltage values associated with different lead types. Trial stimulator 102 may then determine the lead type based on the comparison between measured voltage and stored voltage.

Autonomous lead detection may improve the efficiency and control of programming stimulation therapy delivery for trial stimulator 102. For example, trial stimulator 102 may be configured to automatically limit a number of stimulation programming options available via programmer 108, limit or select one or more stimulation parameter values, or select different programs according to which the trial stimulator can deliver stimulation via stimulation lead 106 based on the type of the lead detected by the device.

As with trial stimulator 16 of FIG. 1, trial stimulator 102 may commonly be secured to the body of patient 104 in a position that makes manipulation of controls integral with the stimulator inconvenient or impractical. For example, trial stimulator 102 may be secured to the back of patient 104 adjacent the waste line of the patient. As such, the vast majority of interaction with and control of trial stimulator 102 is executed by users via electronic programmer 108, which wireless communicates with the stimulator. Trial stimulator 102 does include, however, a single user interface, button 124 integral with the stimulator. Button 124 is conveniently located on one of the two larger faces of trial stimulator 102, e.g. in the center of top half 120*a* of housing 120 as illustrated in FIG. 4A, to make the control easier for patient 104 to locate. Additionally, button 124 may include structural features to make it easier to locate, like a raised edge around the perimeter of the button or a surface finish or coating or texture that differs from the other surfaces of trial stimulator 102. Button 124 is employed for two important functions that may not be best executed by programmer 108. In particular, button 124 is configured to cause trial stimulator 102 to be capable of wireless communication with programmer 108 and to turn off stimulation being delivered by the trial stimulator, e.g., in the event that patient 104 wishes to cease stimulation quickly without accessing a feature-rich user interface via programmer 108 or because programmer 108 is unavailable.

Trial stimulator 102 is configured to be disposed of, i.e., discarded after a single trial with one patient, e.g. patient 104. As such, trial stimulator 102 may be sterilized prior to use in a trial and may be arranged within a sterile field during surgery and intraoperative testing of the stimulator. Because trial stimulator 102 is within the sterile field during surgery, the stimulator may encounter blood and other bodily fluids. Additionally, there may be instances in which trial stimulator 102 is subject to off-label uses by a patient, including showering or bathing with the device. As such, in one example, trial stimulator 102 is configured to resist ingress of liquid into the device.

In some examples, trial stimulator 102 may not be hermetically sealed, as achieving a hermetic seal may be too great a cost for a disposable device like disposable trial stimulator 102. Trial stimulator 102 may, however, employ a number of techniques to resist ingress of liquid into the device. In one example, housing 120 of trial stimulator 102 is configured to resist ingress of liquid into an interior chamber defined by the housing. For example, housing 120 may include a number of sections that are connected to one another to define one or more closed chambers in which various components of trial stimulator 102 are arranged. In one example, different sections of housing 120 are connected by ultrasonic welds that are configured to resist ingress of liquids into the interior chamber(s) of trial stimulator 102. Housing 120 of stimulator 102 includes top half 120a and bottom half 120b. Top half 120a of housing 120 includes lead coupler doors 128 and 130. In one example, the junction between top half 120a including doors 128 and 130 and bottom half 120b of housing 120 may include a gasket that is configured to seal lead coupler 122 inside doors 128 and 130 in order to resist ingress of liquids into the lead coupler.

Trial stimulator 102 may include a battery bay including a cavity and door as described above with reference to stimulator 16 of system 10. In such cases, the interface between the battery bay door and housing 120 of trial stimulator 102 may be sealed with a gasket that is configured to resist ingress of liquids into the cavity of the battery bay.

Example disposable trial stimulator 102 of FIGS. 3 and 4A and 4B may include a number of additional features. In one example, trial stimulator 102 includes a diagnostics module configured to automatically cease delivery of stimulation when stimulation leads 106 are disconnected from the trial stimulator. Additionally, the diagnostic module may be configured to monitor stimulation intensity delivered by trial stimulator 102 via leads 106 and generate an alert when the stimulation intensity delivered by trial stimulator 102 does not equal a programmed stimulation intensity, e.g. stored in memory of stimulator 102 and/or programmer 108.

For example, stimulation leads 106 may include additional conductors that function as resistors at the connection with trial stimulator 102 via lead coupler 122. The diagnostics module of trial stimulator 102 may then be configured to detect the presence or absence of this resistor, e.g., by delivering current across the resistor from a power source of the stimulator. In the event, the resistance of the additional conductor is not detected, the diagnostic module of trial stimulator 102 may, e.g., automatically turn off stimulation and log an error in memory of the device. Trial stimulator 102 may also generate a visual, audible, or tactile alert or communicate with programmer 108 to cause the programmer to generate an alert.

With regard to monitoring stimulation intensity, a stimulation engine of trial stimulator 102 may be configured to measure the actual output energy of stimulation delivered by stimulator 102. In the event the actual stimulation output does not equal the programmed stimulation, an error may be generated and logged and, in some examples, trial stimulator 16 may generate an alert. Depending on the nature of the stimulation error, e.g., the magnitude of the discrepancy between programmed stimulation intensity and actual output or in the event stimulation intensity is detected that is outside of a hard limit set by physician programming, a diagnostic module of trial stimulator 102 may prevent stimulation. In another example, trial stimulator 102 may detect is if the impedance in stimulation leads 106 is either too low or too high and, e.g., trigger an alert as appropriate.

In one example, a diagnostic module of trial stimulator 102 is also configured to detect whether doors 128 or 130 are open, e.g. via a circuit including a switch that is normally closed or open in the door open or closed state. In the event the diagnostic module of trial stimulator 102 detects that either door 128 or 130 is open, in one example, trial stimulator 102 may be configured to turn off stimulation being delivered at the time.

Figure 5:
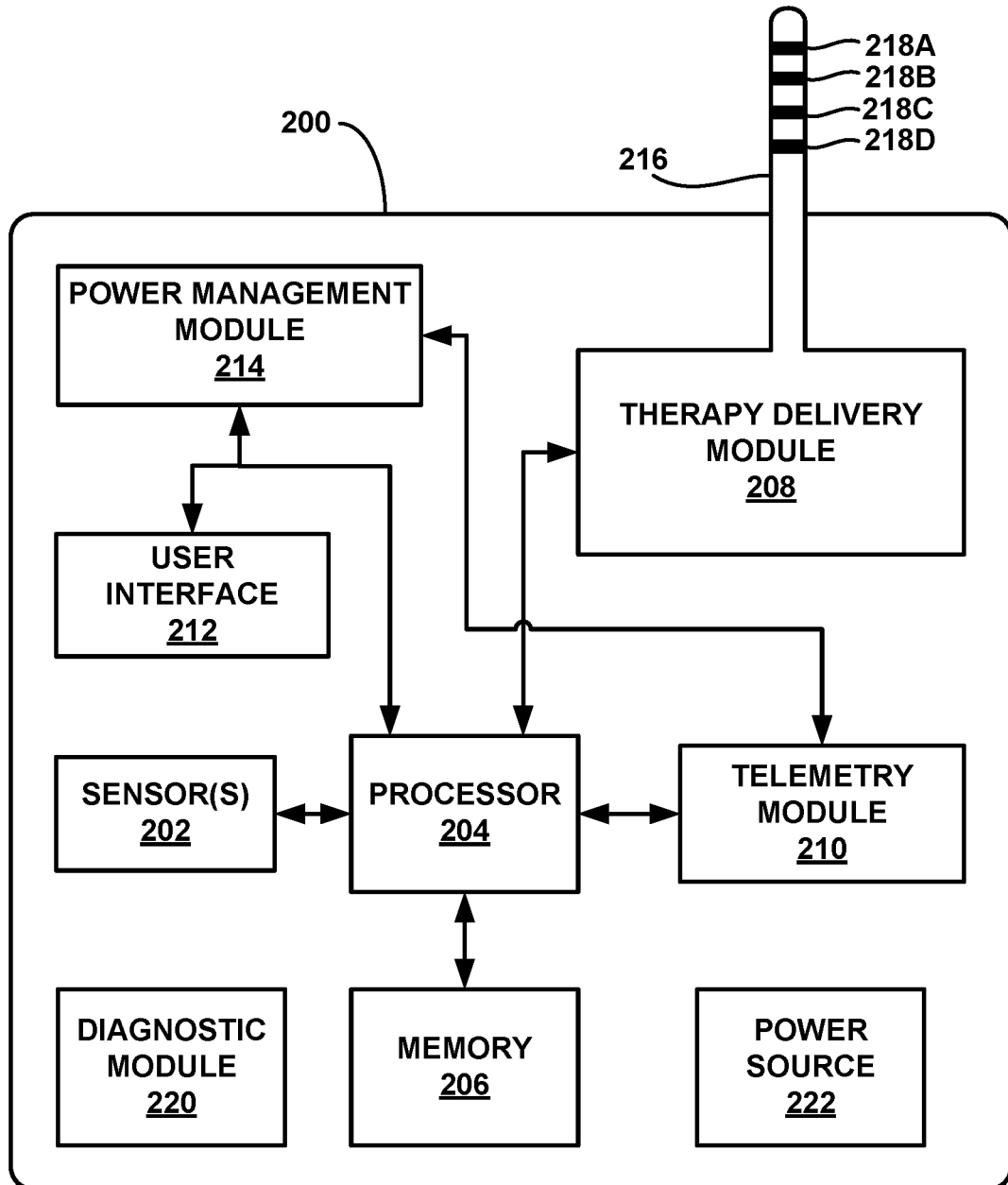
FIG. 5 is a functional block diagram illustrating an example configuration of the implantable medical device (IMD) of the systems shown in FIGS. 1 and 2.

FIG. 5 is a functional block diagram illustrating example components of an example disposable trial stimulator 200 according to this disclosure. The configuration and componentry of trial stimulator 200 may be implemented in a number of different types of trial stimulation systems, including, e.g., trial stimulator 16 of system 10 of FIG. 1 and trial stimulator 102 of system 100 of FIG. 3. However, there may be functional and structural differences depending on which type of system trial stimulator 200 of FIG. 5 is implemented in. For example, the sensors included in trial stimulator 200 may differ if the device is included in a trial stimulation system configured to deliver pelvic floor stimulation, like system 10 of FIG. 1, versus if the device is included in a trial stimulation system configured to deliver SCS therapy, like system 100 of FIG. 3. Moreover, trial stimulator 200 may include additional components if the device is included in a trial stimulation system configured to deliver pelvic floor stimulation, like system 10 of FIG. 1, e.g. an impedance module for monitoring bladder impedance to detect bladder contractions, versus if the device is included in a trial stimulation system configured to deliver SCS therapy, like system 100 of FIG. 3.

In the example of FIG. 5, trial stimulator 200 includes sensor(2) 202, processor 204, memory 206, therapy delivery module 208, telemetry module 210, user interface 212, power management module 214, diagnostic module 220, and power source 222. Processor 204 may be programmed to control a number of components of trial stimulator 200 including therapy delivery module 208 and telemetry module 210, e.g., based on instructions and data stored in memory 206, as well as sensor data from sensor(s) 202. Therapy delivery module 208 is connected to lead 216 including electrodes 218A-218D (collectively "electrodes 218") and is configured to deliver electrical stimulation therapy through electrodes 218 to one or more target tissue sites within a patient. As illustrated in the example of FIG. 5, power management module 214 may be connected to processor 204, telemetry module 210, and user interface 212.

Processor 204 is operably connected to and configured to access information from memory 206 and to control therapy delivery module 208. Components described as processors within trial stimulator 200, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to trial stimulator 200 may be embodied in a hardware device via software, firmware, hardware or any combination thereof.

Memory 206 may store instructions for execution by processor 204, stimulation therapy data, sensor data, e.g. bladder impedance measurements and/or posture state data, and any other information regarding therapy of a patient employing trial stimulator 200. Therapy information may be recorded for long-term storage and retrieval by a user, and the therapy information may include any data created by or stored in trial stimulator 200. Memory 206 may include separate memories for storing instructions, sensor data, therapy adjustment information, program histories, and any other data that may benefit from separate physical memory modules. Memory 206 may include any volatile or non-volatile media, such as a random access memory (RAM), read only memory (ROM), non-volatile RAM (NVRAM), electrically erasable programmable ROM (EEPROM), flash memory, and the like.

Processor 204 controls therapy delivery module 208 to deliver electrical stimulation via electrode combinations formed by electrodes in one or more electrode arrays. For example, therapy delivery module 208 may deliver electrical stimulation therapy via electrodes 218 on lead 216, e.g., as stimulation pulses or continuous waveforms. Therapy delivery module 208 may include stimulation generation circuitry to generate stimulation pulses or waveforms and switching circuitry to switch the stimulation across different electrode combinations, e.g., in response to control signals from processor 204. In particular, processor 204 may control the switching circuitry on a selective basis to cause therapy delivery module 208 to deliver electrical stimulation to selected electrode combinations and to shift the electrical stimulation to different electrode combinations in a various directions when the therapy is delivered to different locations within a patient.

Therapy delivery module 208 of example disposable trial stimulator 200 may be configured to deliver current or voltage controlled stimulation via various electrodes of one or more electrode arrays, including, e.g. different combinations of electrodes 218 on lead 216. In one example, therapy delivery module 208 may include multiple current sources to drive more than one electrode combination at one time.

In one example in which therapy delivery module 208 is configured to deliver current controlled stimulation and includes multiple current sources, therapy delivery module 208 includes a stimulation generator including a voltage supply, a stimulation control module, and a current regulator array. The voltage supply of therapy delivery module 208 may receive operating power from power source 222. In turn, the voltage supply of therapy delivery module 208 may provide a supply voltage to current regulators in the current regulator array. The voltage supply may provide a high supply voltage ($V_{HIGH}$) and a low supply voltage ($V_{LOW}$). The high supply voltage may be coupled to a regulated current source as a supply voltage. The low supply voltage may be coupled to a regulated current sink as a supply voltage. The supply voltage level may be the voltage level used by the current regulator to maintain regulation of the pulse current level. The high and low supply voltages may be positive and negative voltages, respectively, supplied by the voltage supply of therapy delivery module. The high supply voltage $V_{HIGH}$ may be used as a high reference voltage level for a current source, and the low supply voltage $V_{LOW}$ may be used as a low reference voltage level for a current sink. As an example, $V_{HIGH}$ may have a voltage level of approximately +1 V to +10 V, and $V_{LOW}$ may have a voltage level of approximately −1 V to −10 V.

In one example, therapy delivery module 208 includes a stimulation control module that is configured to control the current regulator array to source and sink regulated current stimulation pulses via selected combinations of electrodes 218 on lead 216. The stimulation control module may be implemented in hardware, software, or combinations thereof, including, e.g., one or more microprocessors, microcontrollers, digital signal processors (DSPs), application-specific integrated circuits (ASICs), field-programmable gate arrays (FPGAs), or other integrated or discrete logic circuitry. In operation, the stimulation control module of therapy delivery module 208 may control delivery of electrical stimulation according to one or more programs that specify stimulation parameters such as electrode combination, electrode polarity, stimulation current pulse amplitude, pulse rate, and/or pulse width. Programs may be defined by a user via an external programmer and downloaded to trial stimulator 200 for use by the stimulation control module of therapy delivery module 208.

In one example, the current regulator array of therapy delivery module 208 may include a plurality of regulated current sources and sinks, each of which may be coupled to a respective electrode, e.g. a respective one of electrodes 218. A current regulator may function as either a current source or sink, e.g., by including a source and sink in parallel or by otherwise being selectively configurable to operate as either a source or a sink. For convenience, however, the term "current regulator" may be used in this disclosure to refer generally to either a source or sink. Hence, each of the current regulators in the current regulator array of therapy delivery module 208 may operate as a regulated current source that delivers stimulation via a corresponding one of electrodes 218A-218D or a regulated current sink that receives current from a corresponding one of electrodes 218A-218D.

Each current regulator of the current regulator array of therapy delivery module 208, in one example, may be selectively activated to source or sink current via one of electrodes 218 coupled to the regulator, in which case the electrode is considered active, or deactivated to provide a high impedance connection for the electrode, in which case the electrode may be considered inactive. Hence, each electrode 218 may function as a regulated anode or regulated cathode by connection to a regulated current source or regulated current sink, or function as a high impedance node that may not source or sink a significant amount of current. In some examples, the stimulation control module of therapy delivery module 208 may selectively activate current regulators in the current regulator array to configure electrodes 218 in unipolar, bipolar or multipolar electrode configurations.

In some examples, pulse widths and pulse rates may be selectively controlled by the stimulation control module of therapy delivery module 208 by selectively activating current regulators in the current regulator array, e.g., on a pulse-by-pulse basis, at selected times and for selected durations. The current regulator array of therapy delivery module, in some examples, may also control the shape of the pulses to control the rise time, overshoot, or overall shape (triangle versus square). In addition, the stimulation control module of therapy delivery module 208 may selectively control individual regulated current sources or sinks in the current regulator array to deliver stimulation current pulses via the selected electrodes with desired current levels.

In some examples, therapy delivery module 208 is configured to simulate voltage controlled stimulation with a current controlled stimulation engine. For example, therapy delivery module 208 may be configured to vary the current level of the stimulation delivered based on changing impedance levels in the target tissue being stimulated in order to deliver stimulation at a substantially constant voltage amplitude. In one example, therapy delivery module 208 may include voltage measurement circuitry and a current source that are employed to measure tissue impedance levels, which may be employed to vary current to simulate voltage controlled stimulation. Therapy delivery module 208 may also include an oscillator (not shown) or the like for producing an alternating signal, as is known. In one example, therapy delivery module 208 may periodically control the current source to source an electrical current signal through an electrode, on of electrodes 218 not being used for stimulation delivery and sink the electrical current signal through another o electrodes 218 not being used for stimulation delivery. Therapy delivery module 208 may also include voltage measurement circuitry 62 for measuring the voltage between the source and sink electrodes. The voltage measurement circuitry may, e.g., include sample and hold circuitry or other suitable circuitry for measuring voltage amplitudes. Therapy delivery module may determine an impedance value from the measured voltage values received from the voltage measurement circuitry and may adjust the current controlled stimulation levels based on the impedance to simulate stimulation delivered at a substantially constant voltage amplitude. Therapy may delivered in this mode and other stimulation modes via unipolar, bipolar, or multipolar electrode combinations.

An exemplary range of electrical stimulation parameters that may be effective in treating chronic pain, e.g., when applied to a spinal cord of a patient by therapy delivery module 208 of trial stimulator 200, are listed below. While stimulation pulses are described, stimulation signals may be of any of a variety of forms such as sine waves or the like. Stimulation parameters are presented below for purpose of example, but without limitation.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 milliamps (mA) and approximately 50 mA. In other examples, a voltage amplitude may define the intensity of stimulation delivered to a patient. For example, the range of voltage amplitude may be between approximately 0.1 volts and approximately 50 volts, more preferably between approximately 0.5 volts and approximately 20 volts, and still more preferably between approximately 1 volt and approximately 10 volts.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 Hz to approximately 1200 Hz, such as approximately 5 Hz to approximately 250 Hz, or approximately 30 Hz to approximately 185 Hz, and a pulse width in the range of approximately 10 microseconds and 5000 microseconds, such as between approximately 60 microseconds and approximately 1000 microseconds, between approximately 60 microseconds and approximately 450 microseconds, or between approximately 60 microseconds and approximately 150 microseconds. Amplitude ranges such as those described above with reference to SCS, or other amplitude ranges, may be used for different DBS applications. Additionally, different stimulation parameter values may be employed for other conditions, including, e.g., to treat various pelvic floor disorders including urgency and urinary incontinence.

Telemetry module 210 may enable wireless telemetry between trial stimulator 200 and one or more other electronic devices, including, e.g., an electronic programming device. Telemetry module 210 may enable wireless communications, including, via radio frequency (RF) communication or proximal inductive interaction of trial stimulator 200 with another electronic device. Telemetry module 210 may send information to and receive information from another device on a continuous basis, at periodic intervals, at non-periodic intervals, or upon request from trial stimulator 200 or an electronic programmer. To support RF communication, telemetry module 210 may include appropriate electronic components, such as amplifiers, filters, mixers, encoders, decoders, and the like. Additionally, telemetry module 210 may be configured to communicate via various wireless communication standards and/or protocols, including, e.g., the Bluetooth wireless communication standard.

Example disposable trial stimulator 200 includes user interface 212 for facilitating user interaction with the stimulator. As explained above, one disadvantage of current trial stimulation systems is the manner in which users interact with the system to control stimulation therapy or otherwise interact with the trial stimulator. In some current systems, the trial stimulator includes a number of user input/output controls that are necessary for operation of the system. However, as the trial stimulator in some such systems is commonly held or secured to the back of the patient, it is inconvenient or impractical for the patient to interact with the I/O devices integral with the stimulator. The inclusion of I/O devices integral with the trial stimulator also prevents maintaining the sterile field during surgery, as it may be necessary to interact with such devices during intraoperative testing of the stimulator. Additionally, some current trial stimulation systems utilize programming devices for modulating the therapy, which, while separate from the trial stimulator, must nevertheless be directly next to or very near the stimulator to communicate with it. Again, due to the placement of the trial stimulator on or near the back of the patient, such programming devices are inconvenient or impractical to use.

In view of the foregoing challenges with current trial stimulation systems, in one example, trial stimulator 200 includes a single user interface 212, including, e.g., a button like button 30 of trial stimulator 16 of FIG. 1 or button 124 of trial stimulator 102 of FIG. 3. In such cases, user interface 212 may be configured to cause trial stimulator 200 to be capable of wireless communications with an electronic programming device and to turn off stimulation being delivered by the trial stimulator. In one example, depending on the operational state of trial stimulator 200 a single input to user interface 212 will either cause trial stimulator 200 to be capable of wireless communications with an electronic programming device or will cause the trial stimulator to stop delivering stimulation to the patient. For example, in the event trial stimulator 200 is powered off or is in a lower power operating mode and is not currently delivering stimulation, input to user interface 212 may cause trial stimulator 200 to be capable of communications with an external programmer device. In one example, input to user interface 212 may cause processor 204 to control telemetry module 210 to transmit signals requesting communication with a communication system with any properly configured programming devices, or with a particular device, within range of the signals transmitted by telemetry module 210. In another example, input to user interface 212 may cause processor 204 to control telemetry module 210 to listen for signals requesting communications from an electronic programming device within range of trial stimulator 200. In one example, input to user interface 212 may directly affect operation of telemetry module 210 to facilitate communication with a programming device without going through processor 204.

In the event that therapy delivery module 208 of trial stimulator 200 is currently delivering stimulation, input to user interface 212 may cause processor 204 to stop delivering stimulation. For example, input to user interface 212 while therapy delivery module 208 of trial stimulator 200 is delivering stimulation may cause processor 204 to control therapy delivery module 208 to cease delivering stimulation but may not completely power off trial stimulator 200. In another example, input to user interface 212 may cause processor 204 to completely power off trial stimulator 200.

Trial stimulator 200 also includes power management module 214, which is connected to processor 204, telemetry module 210, and user interface 212. Power management module 214 may be configured to control trial stimulator 200 to operate in a plurality of power consumption modes. In one example, power management module 214 is configured to control trial stimulator 200 to operate in a shelf low-power consumption mode and an operational full-power mode. In one example, power management module 214 may be configured to transition trial stimulator 200 from the shelf low-power consumption mode to the operational full-power mode during initial intraoperative set-up and programming of the trial stimulator.

In one example, trial stimulator 200 is shipped in the shelf low-power consumption mode, in which all of the components of trial stimulator 200 except power management module 214 are not receiving power from power source 222. Power management module 214 may be directly connected to user interface 212 of trial stimulator 200. In one example, when a user is ready to put trial stimulator 200 into a full-power consumption mode, the user may interact with user interface 212, which may, in turn, transmit a signal to power management module 214. Power management module 214 may then function to cause power source 222 to deliver power to one or more of the components of trial stimulator 200, including, e.g. sensors 202, processor 204, memory 206, therapy delivery module 208, telemetry module 210, and diagnostic module 220.

In another example, trial stimulator 200 is shipped in the shelf low-power consumption mode, in which all of the components of trial stimulator 200 except power management module 214 and telemetry module 210 are not receiving power from power source 222. In such an example, either a signal from an external device, e.g. an electronic programming device to telemetry module 210 or input to user interface 212 may cause power management module 214 to cause power source 222 to deliver power to one or more of the other components of trial stimulator 200, including, e.g. sensors 202, processor 204, memory 206, therapy delivery module 208, and diagnostic module 220. For example, input to user interface 212 may cause power management module 214 to transition trial stimulator 200 to a full power mode in which all components, including, e.g., sensors 202, processor 204, memory 206, therapy delivery module 208, and diagnostic module 220 receive power from power source 222. In another example, a near field telemetry signal, e.g., from an electronic programming device to telemetry module 214 may to "Wake Up" trial stimulator 200 such that power management module 214 transitions stimulator 200 to a full power mode in which all components, including, e.g., sensors 202, processor 204, memory 206, therapy delivery module 208, and diagnostic module 220 receive power from power source 222.

Trial stimulator 200 also includes diagnostic module 220. Diagnostic module 220 may be configured to perform a number of diagnostic functions autonomously. For example, diagnostic module 220 may be configured to monitor stimulation intensity delivered by therapy delivery module 208 of trial stimulator 200 via electrodes 218 on lead 216 and generate an alert when the stimulation intensity delivered by therapy delivery module 208 does not equal a programmed stimulation intensity, e.g. stored in memory 206 of stimulator 200 and/or memory of an electronic programmer in communication with stimulator 200.

In one example, diagnostic module 220 may also be configured to automatically cease delivery of stimulation when stimulation lead 216 is disconnected from trial stimulator 200 and detect the type of lead 216 connected to stimulator 200. In some examples, electrical connections between stimulation lead 216 and trial stimulator 200 may be provided for reasons other than connecting stimulation electrodes 218 to therapy delivery module 208 of stimulator 102. In one example, the connection between lead 216 and trial stimulator 200 may include an electrical contact that is configured to connect with a conductor of stimulation lead 216 in order to close a circuit, e.g., included in diagnostic module 220 that is configured to facilitate autonomous detection of the type of lead connected to stimulator 200. For example, an electrical contact may connects a conductor of stimulation lead 216 to a controlled current source of therapy delivery module 208 that is configured to deliver a particular amount of current across the lead conductor. The lead detection circuit of diagnostic module 220 with the controlled current source included in therapy delivery module 208 may be configured to measure the voltage drop across the lead conductor. Diagnostic module 220 may then calculate the resistance of the conductor of lead 216 based on the delivered current and the voltage. Diagnostic module 220 may compare the actual resistance of the conductor of the stimulation lead to a plurality of resistances associated with a plurality of lead types, e.g. stored in memory 206 of trial stimulator 200 and/or memory of an electronic programmer in communication with stimulator 200.

Autonomous lead detection may improve the efficiency and control of programming stimulation therapy delivery for trial stimulator 200. For example, diagnostic module 220 or processor 204 of trial stimulator 200 may be configured to automatically limit at least one of a number of stimulation programming options available for programming via an electronic programmer and one or more stimulation parameter values according to which therapy delivery module 208 of trial stimulator 200 can deliver stimulation via stimulation lead 216 based on the type of the lead detected by the device.

Power source 222 delivers operating power to the components of trial stimulator 200. Power source 222 may include a battery and a power generation circuit to produce the operating power. In some examples, the battery may be rechargeable to allow extended operation. Recharging may be accomplished through proximal inductive interaction between an external charger and an inductive charging coil within trial stimulator 200. In other examples, power source 222 may include one or more primary source batteries, including, e.g. one or more commercially available batteries like AAAA dry cell alkaline batteries.

Figure 6:
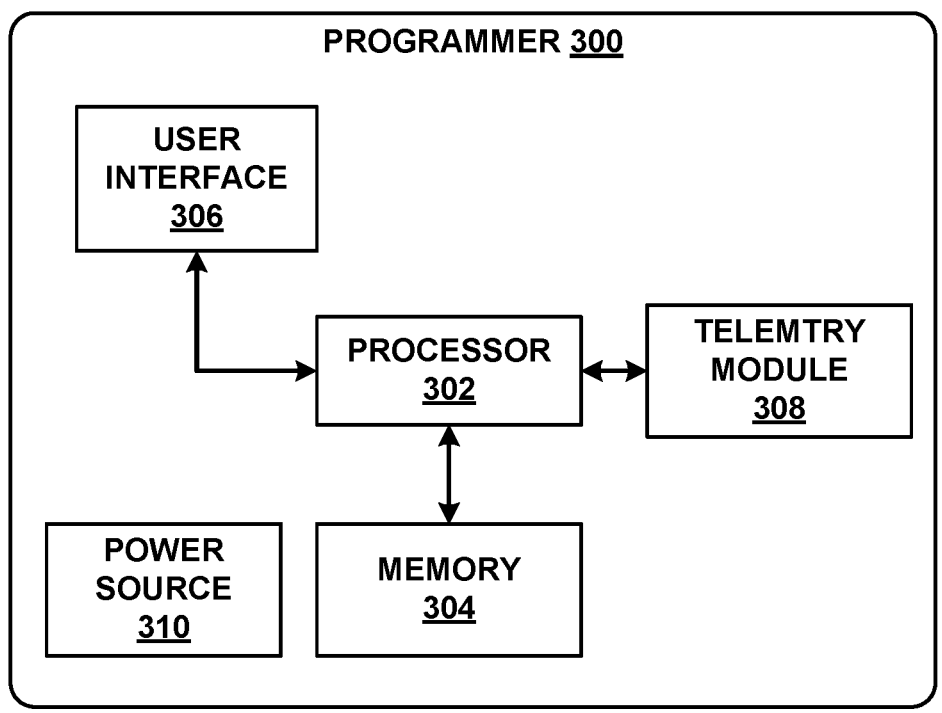
FIG. 6 is a functional block diagram illustrating an example configuration of the external programmer of the systems shown in FIGS. 1 and 2.

FIG. 6 is a functional block diagram illustrating example components of electronic programmer 300. While programmer 300 may generally be described as a hand-held computing device, the programmer may be a notebook computer, a cell phone, or a workstation, for example, or any other electronic device configured for wireless communications with a trial stimulator in accordance with this disclosure. As illustrated in FIG. 6, external programmer 300 may include a processor 302, memory 304, user interface 306, telemetry module 308, and power source 310. Memory 304 may store program instructions that, when executed by processor 302, cause processor 302 to provide the functionality ascribed to programmer 300 throughout this disclosure.

In some examples, memory 304 may further include programs, program groups, and stimulation parameters defining stimulation therapy that may be delivered by a trial stimulator, similar to those stored in memory 206 of trial stimulator 200. The therapy programs or other instructions stored in memory 304 may be downloaded into memory 206 of trial stimulator 200 via telemetry modules 210 and 308. Memory 304 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like.

Processor 302 can take the form of one or more processors such as one or more microprocessors, DSPs, ASICs, FPGAs, programmable logic circuitry, or the like, and the functions attributed to processor 302 herein may be embodied as hardware, firmware, software or any combination thereof. Processor 302 may control or otherwise interact with components of programmer 300, including, e.g., memory 304, user interface 306, and telemetry module 308, to perform various functions related to programming a disposable trial stimulator according to this disclosure. For example, processor 302 may receive input from a user like a clinician via user interface 306 that defines one or more therapy parameters and/or programs, which processor then stores in memory 304 and, in some cases, controls telemetry module 308 to transmit to a trial stimulator like stimulator 200 of FIG. 5.

User interface 306 may include a button or keypad, lights, a speaker for voice commands, and a display, such as a liquid crystal (LCD). In some examples, such as with example programmers 24 and 108 of FIGS. 1 and 3, respectively, user interface 306 may include a touch screen display. As discussed in this disclosure, processor 302 may present and receive information relating to stimulation therapy delivered by a trial stimulator via user interface 306. For example, processor 302 may receive patient input via user interface 306. The patient input may be entered, for example, by pressing a button on a keypad or selecting an icon from a touch screen. For the example of pelvic floor stimulation, patient input may include, but is not limited to, input that indicates an urge felt by the patient, a leakage incident experienced by the patient, an imminent voiding event predicted by the patient, or a voluntary voiding event to be undertaken by the patient. Patient input may also include indications of the efficacy of therapy delivered by a trial stimulator at various times during a stimulation trial. Additionally, as noted above, processor 302 may receive input from a clinician via user interface 306 that is related to the programming or interaction with a trial stimulator according to this disclosure.

Telemetry module 308 supports wireless communication between a trial stimulator, e.g. trial stimulator 200 and external programmer 300 under the control of processor 302. Telemetry module 308 may also be configured to communicate with another computing device via wireless communication techniques, or direct communication through a wired connection. Telemetry module 308 may be substantially similar to telemetry module 210 described above with reference to trial stimulator 200 of FIG. 5, providing wireless communication via an RF or proximal inductive medium. In some examples, telemetry module 308 may include an antenna, which may take on a variety of forms, such as an internal or external antenna. An external antenna that is coupled to programmer 300 may correspond to a programming head that may be placed over trial stimulator 200. Examples of local wireless communication techniques that may be employed to facilitate communication between programmer 300 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer 300 without needing to establish a secure wireless connection.

Power source 310 of programmer 300 delivers operating power to the components of programmer 300. Power source 310 may include a battery, for example a rechargeable or primary source battery. Recharging may be accomplished by using an alternating current (AC) outlet or through proximal inductive interaction between an external charger and an inductive charging coil within programmer 300.

Figure 7:
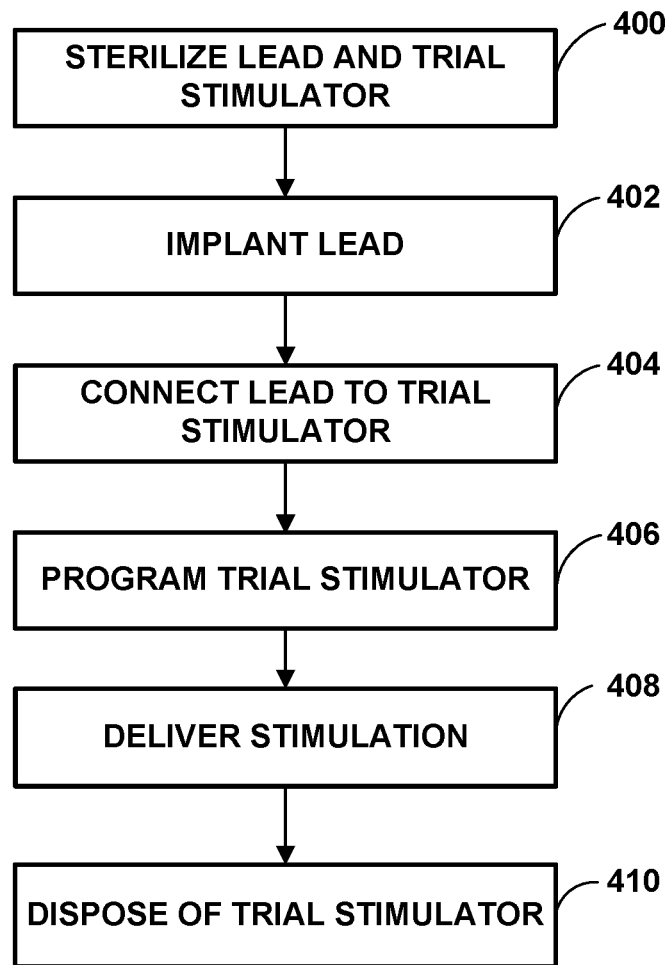
FIG. 7 is a flowchart illustrating an example method of using a disposable trial stimulator.

FIG. 7 is a flowchart illustrating an example method of using a disposable trial stimulator according to this disclosure. The method of FIG. 7 includes sterilizing a percutaneous stimulation lead and a trial stimulator (400), implanting the percutaneous stimulation lead to deliver stimulation to a target tissue location (402), connecting the percutaneous stimulation lead to the disposable trial stimulator (404), programming the trial stimulator to deliver stimulation via the percutaneous stimulation lead (406), delivering stimulation to the target tissue location via the percutaneous stimulation lead with the trial stimulator for a trial period of time (408), and disposing of the trial stimulator after expiration of the trial period of time (410).

The example method of claim 7 includes sterilizing a percutaneous stimulation lead and a trial stimulator (400). For example, trial stimulator 16 and lead 18 of system 10 of FIG. 1 or trial stimulator 102 and leads 106 of system 100 of FIG. 3 may be sterilized. Additionally, in systems like system 10 of FIG. 1, a lead extension like lead extension 22 may also be sterilized along with trial stimulator 16 and lead 18. As noted above, in contrast to current trial stimulation systems including reusable trial stimulators, because example trial stimulators according to this disclosure are configured to be disposed of after a single trial, the trial stimulator and any leads connected thereto may be sterilized prior to implanting the leads. Sterilization of the lead and the disposable trial stimulator in examples according to this disclosure may function to maintain the integrity of the sterile field during surgery and may therefore reduce the risk of potentially harmful microbes traveling into or out of the sterile field, which may, in turn, reduce the risk of complications such as contamination and/or infection. Although the example method of FIG. 7 recites sterilizing and implanting one lead, it is noted that in other examples according to this disclosure multiple leads may be sterilized, implanted, and coupled to a disposable trial stimulator.

In addition to sterilizing a percutaneous stimulation lead and a trial stimulator (400), the method of FIG. 7 includes implanting the percutaneous stimulation lead to deliver stimulation to a target tissue location (402). For example, in system 10 configured to deliver pelvic floor stimulation to treat one of a number of conditions including urgency and urinary incontinence, lead 28 may be implanted in patient 14 through incision 28 and subcutaneously tunneled to arrange electrodes 20 adjacent a pelvic floor nerve or nerves. In another example like system 100 directed to treating chronic pain via SCS, leads 16 may be implanted in patient 104 through incision 110 to arrange electrodes on the leads adjacent spinal cord 112.

The example method of FIG. 7 includes connecting the percutaneous stimulation lead to the disposable trial stimulator (404). In one example, the lead is connected directly to the disposable trial stimulator via a lead coupler integral with the trial stimulator. The lead coupler may be configured to connect a plurality of types of percutaneous stimulation leads directly to the trial stimulator without any intervening lead connection devices. For example, example disposable trial stimulator 102 of FIGS. 3 and 4A and 4B is connected to lead 106 including four electrodes 126A-126D via lead coupler 122. Top half 120a of housing 120 includes two lead coupler doors 128 and 130, which are configured to pivot open to expose lead coupler 122.

Lead coupler 122 of trial stimulator 102 is configured to connect up to four stimulation leads to the disposable stimulator. Opening doors 128 and 130 exposes six slots 134A-134F (collectively "slots 134") included in lead coupler 122. Slots 134 may be substantially the same and configured to receive the same type of stimulation leads or, in other examples, one or more of slots 134 may be different from one another and configured to receive different types of stimulation leads, e.g. slots 134A and 134F with eight contacts are different than slots 134B-134E with four contacts. Each of slots 134 of lead coupler 122 of trial stimulator 102 is configured to connect one stimulation lead to stimulator 102. For example, percutaneous stimulation lead 106 is connected directly to trial stimulator without any intervening lead connection devices via slot 134D of lead coupler 122. Each of slots 134 may include one or more electrical contacts, like contact 136 illustrated with reference to slot 134D in FIG. 4A. Stimulation leads, like lead 106 may be press fit into slots 134, e.g., press fit latterly into slots 134 when doors 128 and 130 are open and may be configured with exposed electrical conductors arranged along the end of the lead received by the slots, e.g. the proximal end of the lead, such that the lead conductors contact the electrical contacts in slots 134. Stimulation leads, like lead 106 may thus be electrically connected to trial stimulator 102 such that stimulator 102 may deliver stimulation therapy or sense various parameters related to a patient via electrodes arranged at the distal end of the lead, e.g. electrodes 126A-126D and connected to the lead conductors contacting the electrical contacts of slots 134.

In another example, the percutaneous stimulation lead may be connected to the trial stimulator (404) indirectly. For example, lead 18 of system 10 of FIG. 1 may be connected to lead extension 22 via adaptor 26 and lead extension 22 may be connected to trial stimulator 16.

In some examples according to this disclosure, the trial stimulation to which the percutaneous lead(s) is connected (404) in the example method of FIG. 7 includes a single user interface integral with the trial stimulator. For example, trial stimulator 16 of FIG. 1 includes button 30 and trial stimulator 102 of FIG. 3 includes button 124 as the single user interface integral with the respective disposable trial stimulators according to this disclosure. The single user interface, e.g. user interface 212 of trial stimulator 200 of FIG. 5 may be configured to cause stimulator 200 to be capable of wireless communications with an electronic programmer and to turn off stimulation being delivered by the trial stimulator in the manner described above with reference to FIG. 5.

In addition to connecting the percutaneous stimulation lead to the disposable trial stimulator (404), the example method of FIG. 7 includes programming the trial stimulator to deliver stimulation via the percutaneous stimulation lead (406) and delivering stimulation to the target tissue location via the percutaneous stimulation lead with the trial stimulator for a trial period of time (408). In some examples according to this disclosure programming of a disposable trial stimulator, including intraoperative set-up and programming of such devices will be executed by an electronic programming device via wireless communications between the programmer and stimulator. In other words, programming of disposable programming devices according to this disclosure does not necessitate any direct interaction with user interface controls or other I/O devices integral with the stimulator and thus the stimulator may be kept within the sterile field during surgery. In one example, after communications between trial stimulator 16 and programmer 24 have been initiated, e.g., by pressing button 30, trial stimulator 16 may be programmed to delivery pelvic floor stimulation to patient 14 via electrodes 20 on lead 18 by programmer 24. In another example, trial stimulator 102 may be programmed to deliver SCS to patient 104 via electrodes on leads 106 by programmer 108, in the example of FIG. 3.

After the trial stimulator has been set-up and programmed, stimulation is delivered by the stimulator to the target tissue location via the percutaneous stimulation lead for a trial period of time (408). For example, processor 204 of trial stimulator 200 controls therapy delivery module 208 to deliver therapy via one or more of electrodes 218 on lead 216. In one example, therapy delivery module 208 of example disposable trial stimulator 200 may be configured to deliver current controlled stimulation via various electrodes of one or more electrode arrays, including, e.g. different combinations of electrodes 218 on lead 216. In one example, therapy delivery module 208 includes a stimulation generator including a voltage supply, a stimulation control module, and a current regulator array and is configured to drive more than one electrode combination at one time. Additionally, as described above, in one example, therapy delivery module 208 may be configured to simulate voltage controlled stimulation with a current controlled stimulation engine. For example, therapy delivery module 208 may be configured to vary the current level of the stimulation delivered via electrodes 218 on lead 216 based on changing impedance levels in the target tissue being stimulated in order to deliver stimulation at a substantially constant voltage amplitude.

Chronic implantation of a pulse generator and lead for delivering stimulation therapy to a patient may be preceded by a trial period of time. The trial period ordinarily has a prescribed maximum duration, but sometimes is exceeded by the patient or the physician. During the trial period, a clinician evaluates the efficacy of stimulation in alleviating the patient's disorder to determine whether the patient is a good candidate for chronic implantation. Examples according to this disclosure, including the example method of FIG. 7, are directed to delivering electrical stimulation therapy via a disposable trial stimulator during a trial stimulation period of time, which may last, e.g., 1-3 weeks.

After expiration of the trial period of time, the example method of FIG. 7 includes disposing of the trial stimulator (410). For example, lead 16 of system 10 of FIG. 1 may be disconnected from trial stimulator 16 and removed from patient 14 or continue to be employed in additional trials or as part of a chronic stimulation system. Trial stimulator 16, however, is disposed of after the single stimulation trial of patient 14. Similarly, in one example, lead 106 of system 100 of FIG. 3 may be disconnected from trial stimulator 102 and removed from patient 104 or employed in additional trials or as part of a chronic stimulation system. Trial stimulator 102, however, is disposed of after the single stimulation trial of patient 104. Disposal of a trial stimulator according to this disclosure generally refers to not reusing the stimulator beyond a single stimulation trial with one patient. Thus, disposal may include discarding of the trial stimulator completely or may include partially or completely recycling the trial stimulator and components thereof.

As described above, examples according to this disclosure include devices for securing a disposable trial stimulator to the body of a patient, which may function to improve the durability of a trial stimulation system during the trial period and reduce the risk of damage or malfunction to the system due to lead/electrode dislocation and/or off-label uses like showering or bathing with the trial stimulator still secured to the body. FIGS. 8A-8C and 9A-9C are conceptual diagrams illustrating two different example systems for securing a disposable trial stimulator to the body of a patient. In general, however, a system for securing a disposable trial stimulator to a body of a patient includes a patch and a holster. The patch includes a first major surface at least partially covered with an adhesive configured to adhere the patch to the body of the patient. The holster is connected to a second major surface of the patch. The holster is configured to receive the trial stimulator.

Figure 8B:
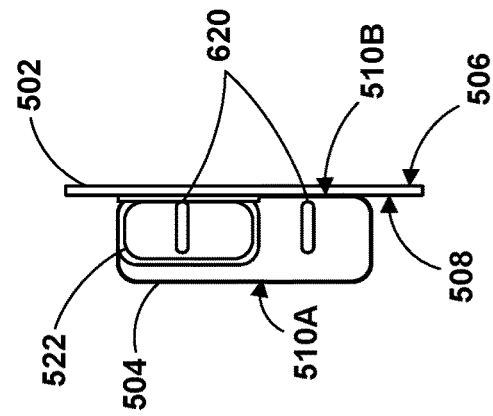
FIGS. 8A-8C are conceptual diagrams illustrating an example system for securing a disposable trial stimulator to the body of a patient.
Figure 8A:
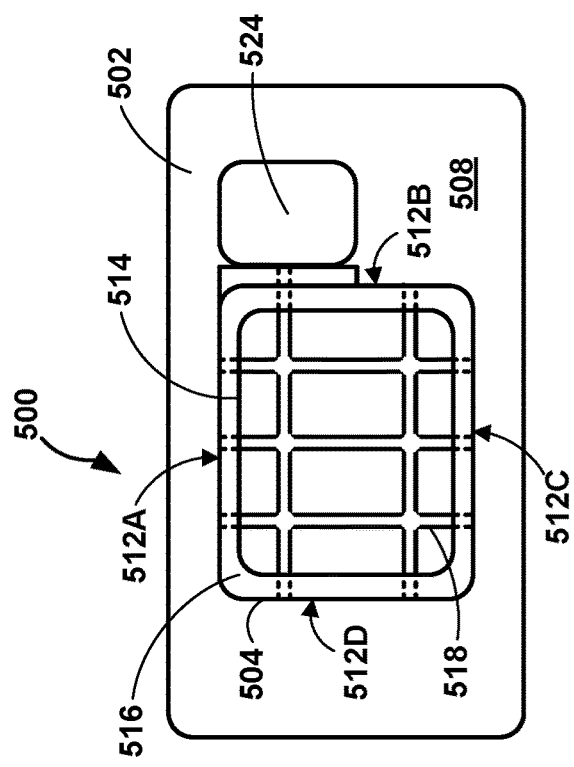
Figure 8C:
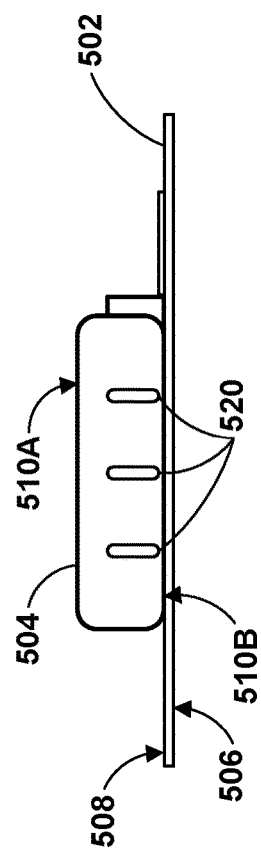

FIGS. 8A-8C are conceptual diagrams illustrating example system 500 for securing a disposable trial stimulator to the body of a patient. In one example, system 500 of FIGS. 8A-8C may be employed to secure trial stimulator 16 of FIGS. 1-2C to the lower back of patient 14. System 500 includes patch 502 and holster 504. Patch 502 includes first major surface 506, which may be at least partially covered with an adhesive configured to adhere the patch to the body of a patient, e.g., to the lower back of patient 14. Holster 504 is connected to second major surface 508 of patch 502 and is configured to receive a disposable trial stimulator according to this disclosure, including, e.g., trial stimulator 16.

Patch 502 is configured to adhere to the skin of a patient. As such, first major surface 506 is at least partially covered with a medical grade adhesive. In one example, first major surface 506 is covered with an acrylic pressure-sensitive adhesive. In one example, the acrylic adhesive employed for first major surface 506 of patch 502 may be similar to the adhesive used on the MED 5719 single coated white embossed non-woven tape manufactured by Avery Dennison of Painesville, Ohio. Patch 502 may be fabricated from a number of materials. In one example, patch 502 comprises a polyethylene terephthalate (PET) non-woven material.

Holster 504 is connected to second major surface 508 of patch 502. As illustrated in the example of FIGS. 8A-8C, holster 504 may be adhered directly to patch 502 with an adhesive between second major wall 510B of holster 504 and second major surface 508 of patch 502. In one example, holster 504 is adhered to patch 502 with double sided tape. For example, holster 504 may be adhered to patch 502 with double sided tape with a first adhesive configured to engage second major surface 508 of patch 502 and a second adhesive configured to engage second major wall 510B of holster 504. In one example, holster 504 is adhered to patch 502 with double coated tape 9731 manufactured by 3M of St. Paul, Minn., which includes a silicone pressure sensitive adhesive coated on one side of a polyester film carrier and a high performance acrylic adhesive coated on the other side of the carrier.

In other examples, holster 504, or another holster according to this disclosure may be connected to patch 502 indirectly. For example, a flexible pouch may be connected to patch 502, e.g. using an adhesive. Holster 504 may then be received in the pouch to secure the holster and the trial stimulator held therein to the body of a patient. In such examples, patch 502 and holster 504 may remain separable.

In FIGS. 8A-8C, holster 504 includes first and second major walls 510A and 510B, respectively, and four minor walls 512A-512D. First and second major walls 510A and 510B are generally rectangular planar walls, each of which includes four edges. Minor walls 512A-512D protrude perpendicular from each of the four edges of second major wall 510B to connect to the four edges of first major wall 510A. First and second major walls 510A and 510B are parallel and offset from each other by minor walls 512A-512D.

First major wall 510A includes aperture 514, which is sized to permit a trial simulator according to this disclosure, like, e.g., trial stimulator 16 to be inserted into holster 504. Aperture 514 is sized such that a majority of first major wall 510A of holster 504 is open for insertion of a trial stimulator, but a rim 516 remains around the perimeter of first major wall 510A that helps to hold the trial stimulator in holster 504. Aperture 514 is sized such that it may expose user interface or other I/O devices of a trial stimulator received by holster 504. For example, aperture 514 is sized to expose button 30 of trial stimulator 16 of FIG. 1.

Second major wall 510B of holster 504 includes grooves 518. Grooves 518 terminate at slots 520 in minor walls 512A-512D. Grooves 518 and slots 520 are configured to channel water and other moisture off of a trial stimulator secured by system 500 and out of holster 504. In the example of FIGS. 8A-8C, holster 504 includes five grooves in second major wall 510B, three extending perpendicular to and between minor walls 512A and 512C and two extending perpendicular to and between minor walls 512B and 512D. In other examples, however, a holster for receiving and securing a trial stimulator according to this disclosure may include more or fewer grooves such as grooves 518 (see, e.g., FIGS. 9A-9C).

Minor wall 512B of holster 504 includes aperture 522, which may be configured to accommodate a lead extension that is coupled to a trial stimulator secured by system 500 in holster 504. For example, aperture 522 may be shaped and sized to accommodate lead extension 22 that is coupled to trial stimulator 16 and includes lead adaptor 26 that is configured to connect extension 22 to a lead, like, e.g., lead 18. In the example of FIGS. 8A-8C, holster 504 also includes pad 524, which may be configured to be interposed between lead extension 22 and patch 502 to prevent or reduce the risk of extension 22 causing irritation of or sores on the skin of a patient.

In one example, holster 504 is a resilient material that is configured to elastically deform in order to insert a trial stimulator into holster 504 including stretching rim 516 of first major wall 510A around the perimeter of the trial stimulator. Holster 504 may be fabricated from a variety of materials, including, e.g., a variety of polymers. For example, holster 504 may be fabricated from a variety of plastics or elastomers. In one example, holster 504 is fabricated from a Class VI silicone with 40A+/−5 durometer hardness.

Figure 9B:
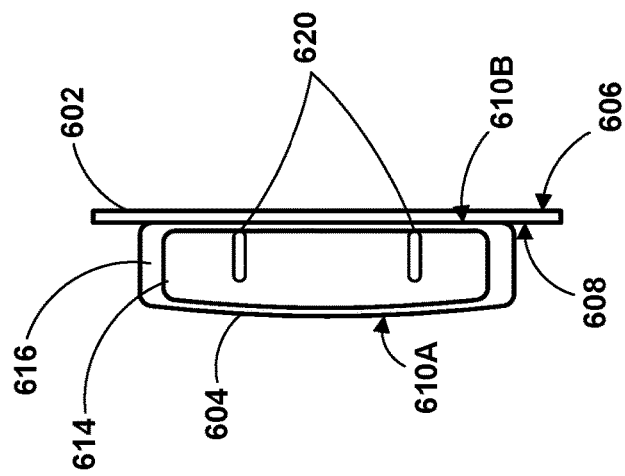
FIGS. 9A-9C are conceptual diagrams illustrating another example system for securing a disposable trial stimulator to the body of a patient.
Figure 9A:
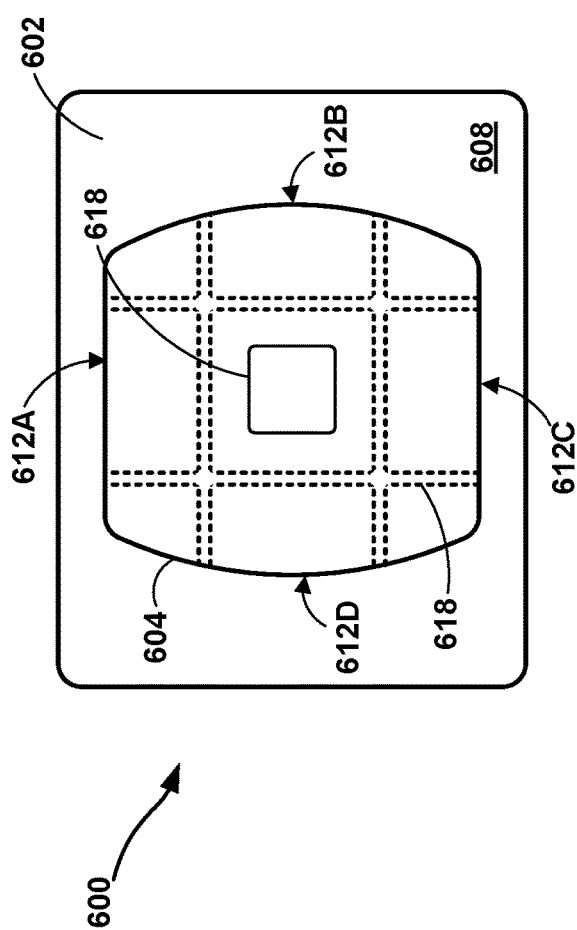
Figure 9C:
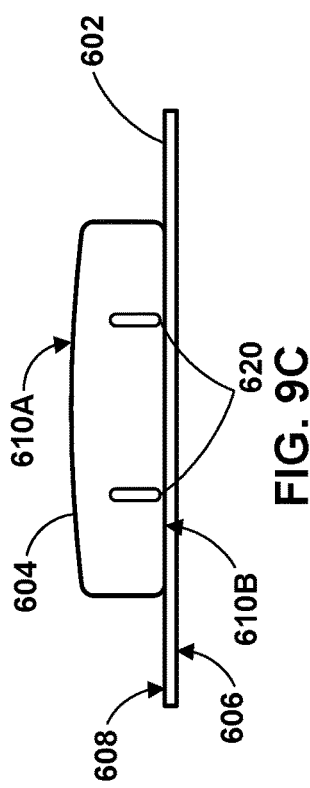

FIGS. 9A-9C are conceptual diagrams illustrating another example system 600 for securing a disposable trial stimulator to the body of a patient. In one example, system 600 of FIGS. 9A-9C may be employed to secure trial stimulator 102 of FIGS. 3, 4A and 4B to the lower back of patient 104. System 600 includes patch 602 and holster 604. Patch 602 includes first major surface 606, which may be at least partially covered with an adhesive configured to adhere the patch to the body of a patient, e.g., to the lower back of patient 104. Holster 604 is connected to second major surface 608 of patch 602 and is configured to receive a disposable trial stimulator according to this disclosure, including, e.g., trial stimulator 102.

System 600 may be substantially similar to system 500 of FIGS. 8A-8C, except in the geometric configuration of holster 604, which is configured to receive a different disposable trial stimulator according to this disclosure, e.g. trial stimulator 102. For example, the materials of patch 602 and holster 604, the manner in which holster 604 is connected to second major surface 608 of patch 602, the adhesives used for adhering first major surface 606 of patch 602 to the body of a patient and adhering holster 604 to second major surface 608 of patch 602 may be similar to such features described above with reference to system 500 of FIGS. 8A-8C.

In FIGS. 9A-9C, holster 604 includes first and second major walls 610A and 610B, respectively, and four minor walls 612A-612D. First and second major walls 610A and 610B are generally rectangular planar walls, each of which includes four edges. Minor walls 612A-612D protrude perpendicular from each of the four edges of second major wall 610B to connect to the four edges of first major wall 610A. First and second major walls 610A and 610B are parallel and offset from each other by minor walls 612A-612D.

Minor wall 612B of holster 604 includes aperture 614, which is sized to permit a trial simulator according to this disclosure, like, e.g., trial stimulator 102 to be inserted into holster 604. Aperture 614 is sized such that a majority of minor wall 612B of holster 604 is open for insertion of a trial stimulator, but a rim 616 remains around the perimeter of minor wall 612B that helps to hold the trial stimulator in holster 604.

In addition to allowing insertion of a trial stimulator, e.g. stimulator 102 into holster 604, aperture 614 also functions to accommodate one or more leads directly or indirectly coupled to holster 604. For example, leads 16 may be directly coupled to trial stimulator 102 via lead coupler 122 integral with stimulator 102 through aperture 614 when stimulator 102 is held within holster 604.

Second major wall 610B of holster 604 includes grooves 618. Grooves 618 terminate at slots 620 in minor walls 612A-612D. Grooves 618 and slots 620 are configured to channel water and other moister off of a trial stimulator secured by system 600 and out of holster 604. In the example of FIGS. 9A-9C, holster 604 includes four grooves in second major wall 610B, two extending perpendicular to and between minor walls 612A and 612C and two extending perpendicular to and between minor walls 612B and 612D. In other examples, however, a holster for receiving and securing a trial stimulator according to this disclosure may include more or fewer grooves such as grooves 618 (see, e.g., FIGS. 8A-8C).

First major wall 610A of holster 604 includes aperture 618. Aperture 618 may be shaped and sized to expose user interface or other I/O devices of a trial stimulator received by holster 604. For example, aperture 618 is sized to expose button 124 of trial stimulator 102 of FIG. 3. Holster 504 and/or holster 604 of FIGS. 8A-8C and 9A-9C, respectively, may include additional apertures to accommodate other interfaces to the respective trial stimulators held by each holster. For example, holster 504 and/or holster 604 may include one or more additional apertures in the major walls or minor walls of the holsters that are sized and shaped to accommodate various I/O devices, including, e.g., a receptacle configured to receive a computer readable storage medium.

Figure 10:
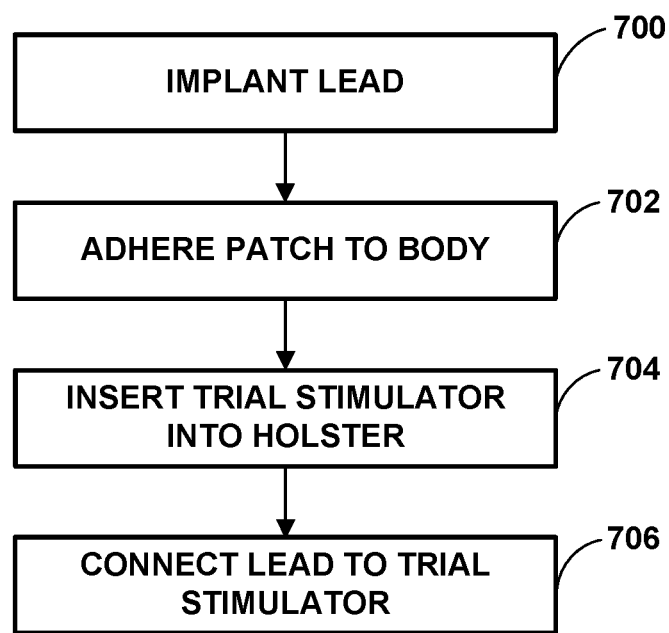
FIG. 10 is a flowchart illustrating an example method of securing a disposable trial stimulator to the body of a patient.

FIG. 10 is a flowchart illustrating an example method of securing a disposable trial stimulator to the body of a patient. The method of FIG. 10 includes implanting a percutaneous stimulation lead to deliver stimulation to a target tissue location (700), adhering a first major surface of a patch at least partially covered with an adhesive to the body of the patient (702). A holster is connected to a second major surface of the patch. The holster is configured to receive the trial stimulator. The method of FIG. 10 also includes inserting the trial stimulator into the holster (704) and connecting the percutaneous stimulation lead to the trial stimulator (706).

For brevity, the example method of FIG. 10 will be described in the context of securing trial stimulator 16 of FIG. 1 to the body of patient 14 employing system 500 of FIGS. 8A-8C. However, in other examples, the method of FIG. 10 may be employed to secure other disposable trial stimulators to the body of a patient. For example, the method of FIG. 10 may be employed to secure trial stimulator 102 of FIG. 3 to the body of patient 104 using system 600 of FIGS. 9A-9C.

The method of FIG. 10 includes implanting the percutaneous stimulation lead to deliver stimulation to a target tissue location (700). For example, in system 10 configured to deliver pelvic floor stimulation to treat one of a number of conditions including urgency and urinary incontinence, lead 28 may be implanted in patient 14 through incision 28 and subcutaneously tunneled to arrange electrodes 20 adjacent a pelvic floor nerve or nerves.

The example method of FIG. 10 also includes adhering a first major surface of a patch at least partially covered with an adhesive to the body of the patient (702). In one example, patch 502 is adhered to the lower back of patient 14. For example, patch 502 may be packaged with a thin plastic film covering the adhesive at least partially covering first major surface 506 of patch 502. A clinician may remove the plastic film from first major surface 506 of patch 502 and press patch 502 against the skin of patient 14, thereby activating the pressure-sensitive acrylic adhesive covering first major surface 506 and adhering system 500 to the patient's body.

In addition to adhering a first major surface of a patch at least partially covered with an adhesive to the body of the patient (702), the method of FIG. 10 also includes inserting the trial stimulator into the holster (704). In one example, trial stimulator 16 is inserted into holster 504. For example, trial stimulator 16 may be inserted through aperture 514 such that when received in holster 504 button 30 is exposed by aperture 514 and coupler 32 is aligned with aperture 522 in minor wall 512B. Holster 504 may be fabricated from a resilient material that is configured to be elastically, e.g. reversibly deformed including stretching rim 516 of first major wall 510A around the perimeter of trial stimulator 16. After holster 504 has been stretched to insert trial stimulator 16 therein, rim 516 around the perimeter of first major wall 510A that helps to hold the trial stimulator in holster 504 regardless of the orientation of holster 504 or system 500 as a whole.

The method of FIG. 10 also includes connecting the percutaneous stimulation lead to the disposable trial stimulator (706). In one example, lead 18 is connected to lead extension 22 via adaptor 26 and lead extension 22 is connected to trial stimulator 16. Aperture 522 in minor wall 512B of holster 504 is sized and shaped to accommodate lead extension 22. In another example, a lead may be connected directly to the disposable trial stimulator held in a holster according to this disclosure via a lead coupler integral with the trial stimulator. The lead coupler may be configured to connect a plurality of types of percutaneous stimulation leads directly to the trial stimulator without any intervening lead connection devices.

Any combination of the foregoing systems and devices may be packaged as a kit. For example, system 10 of FIG. 1 and system 100 of FIG. 3 may be packaged as a kit including at least one lead, and, as appropriate, at least one lead extension, and at least one trial stimulator. Additionally, trial stimulation systems according to this disclosure may be packaged as a kit with systems for securing trial stimulators to the body of a patient, including, e.g. systems like system 500 of FIGS. 8A-8C and system 600 of FIGS. 9A-9C. As such, in one example, at least one of each of trial stimulator 16, lead extension 22, lead 18, and system 500 including patch 502 and holster 504 may be packaged as a kit. In another example, at least one of each of trial stimulator 102, lead 16, and system 600 including patch 602 and holster 604 may be packaged as a kit. In some examples, systems for securing trial stimulators to the body of a patient, including, e.g. systems like system 500 of FIGS. 8A-8C and system 600 of FIGS. 9A-9C may be packaged on their own separate from the trial stimulation system. In some examples, kits may include multiple leads and/or lead extensions including the same or different types of leads and extensions.

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise RAM (e.g., synchronous dynamic random access memory (SDRAM)), ROM, NVRAM, EEPROM, FLASH memory, magnetic or optical data storage media, and the like.

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

Many examples of the disclosure have been described. These and other examples are within the scope of the following claims. Various modifications may be made without departing from the scope of the claims.

What is claimed is:

1. A medical trial stimulation system comprising:
a remote controller;
an external trial electrical stimulator comprising:
a housing that includes a single user control, wherein the single user control comprises one of a button, a rocker switch, a slider switch, or a rotary dial switch, and
a stimulation generator disposed within the housing and configured to generate an electrical signal for stimulation therapy, wherein the electrical signal is current controlled and comprises a pulse rate between 0.5 Hz and 1200 Hz and a pulse width between 10 microseconds and 5000 microseconds; and
at least one lead configured to be connected to the external trial electrical stimulator to deliver the electrical signal as the stimulation therapy;
wherein the single user control is configured to cause: (i) the external trial electrical stimulator to exit a low power mode, in which the external trial electrical stimulator is consuming low power, and enter an operational power mode, and (ii) a telemetry module of the external trial electrical stimulator to be capable of wireless communications with the remote controller;
wherein the stimulation therapy is programmed by the remote controller after wireless communications are established.

2. The system of claim 1, wherein the remote controller is one of a patient controller and a physician controller.

3. The system of claim 1, wherein, when in the low power mode, a power management module of the external trial electrical stimulator is powered on while at least one of the telemetry module and the stimulation generator is powered off, and wherein the single user control, when activated, is configured to cause the external trial electrical stimulator to exit the low power mode and enter the operational power mode by at least delivery of power to at least one of the telemetry module and the stimulation generator.

4. The system of claim 1, wherein the current controlled electrical signal is varied based on an impedance value at one or more electrode.

5. The system of claim 1, wherein the at least one lead is a percutaneous lead.

6. The system of claim 1, wherein the at least one lead is a chronic lead.

7. The system of claim 1, wherein the stimulation generator is configured to generate the electrical signal having pulses comprising a pulse rate between 5 Hz and 250 Hz and a pulse width between 60 microseconds and 450 microseconds.

8. The system of claim 7, wherein the stimulation generator is configured to generate the electrical signal having pulses comprising an amplitude between 0.1 milliamps and 50 milliamps.

9. The system of claim 1, wherein the single user control is configured to cause the external trial electrical stimulator to turn off stimulation being delivered by the external trial electrical stimulator.

10. The system of claim 1, wherein the housing is fabricated from a polycarbonate and ABS polymer blend.

11. An external trial electrical stimulator comprising:
a housing with a single user control, the single user control comprising one of a button, a rocker switch, a slider switch, or a rotary dial switch, wherein the single user control, when activated, causes: (i) the stimulator to exit a low power mode, in which the stimulator is consuming low power, and enter an operational power mode, and (ii) a telemetry module of the stimulator to wirelessly communicate with a remote controller;
a stimulation generator disposed within the housing and being responsive to the remote controller; and
a connector configured to electrically couple the stimulation generator and a lead that is configured to be at least partially implanted, the stimulation generator configured to generate an electrical signal for stimulation therapy via the lead after programming by the remote controller, wherein the electrical signal comprises a pulse rate between 0.5 Hz and 1200 Hz and a pulse width between 10 microseconds and 5000 microseconds.

12. The stimulator of claim 11, wherein the connector directly connects the lead to the stimulation generator.

13. The stimulator of claim 11, wherein the connector comprises a lead extension.

14. The stimulator of claim 11, wherein the lead is one of a percutaneous lead and a chronic lead.

15. The stimulator of claim 11, wherein, when in the low power mode, a power management module of the stimulator is powered on while at least one of the telemetry module and the stimulation generator is powered off, and wherein the single user control, when activated, causes the stimulator to exit the low power mode and enter the operational power mode by at least delivering of power to at least one of the telemetry module and the stimulation generator.

16. A method for delivering electrical stimulation, the method comprising:
    engaging a single user control of an external trial electrical stimulator to: (i) exit a low power mode, in which the external trial electrical stimulator is consuming low power, and enter an operational power mode and (ii) enable wireless communication between the external trial electrical stimulator and a remote controller in order to program the external trial electrical stimulator with the remote controller, the external trial electrical stimulator comprising:
        a housing with the single user control, wherein the single user control comprises one of a button, a rocker switch, a slider switch, or a rotary dial switch
        a stimulation generator disposed within the housing,
        a lead electrically coupled to the stimulation generator; and
    using the remote controller to send a wireless communication to cause the stimulation generator to deliver programmed stimulation therapy via the lead, wherein the stimulation therapy comprises delivery of an electrical signal comprising a pulse rate between 0.5 Hz and 1200 Hz and a pulse width between 10 microseconds and 5000 microseconds.

17. The method of claim 16, further comprising:
    adjusting a level of the electrical signal based on an impedance value at one or more electrode.

18. The method of claim 16, wherein the remote controller is one of a patient controller and a physician controller.

19. The method of claim 16, wherein, when in the low power mode, a power management module of the external trial electrical stimulator is powered on while at least one of a telemetry module of the external trial electrical stimulator and the stimulation generator is powered off, and wherein the single user control, when activated, is configured to cause the external trial electrical stimulator to exit the low power mode and enter the operational power mode by at least delivering power to at least one of the telemetry module and the stimulation generator.

20. The method of claim 16, wherein the electrical signal is a current controlled electrical signal.

21. The method of claim 16, wherein the external trial electrical stimulator is configured to automatically cease stimulation therapy when the lead is disconnected from the stimulation generator.

22. The method of claim 16, wherein engaging the single user control enables requesting a wireless communication from the external trial electrical stimulator to the remote controller or listening to a wireless communication from the remote controller to the external trial electrical stimulator.

23. A medical trial stimulation system comprising:
    a remote controller; and
    an external trial electrical stimulator comprising:
        a housing comprising a button as a single user control, the button configured to cause the external trial electrical stimulator to: (i) exit a low power mode, in which the external trial electrical stimulator is consuming low power, and enter an operational power mode, and (ii) be capable of wireless communications with the remote controller for programming by the remote controller; and
        a stimulation generator disposed within the housing and configured to, after programming by the remote controller, generate an electrical signal for stimulation therapy via an electrode, wherein the electrical signal is current controlled and comprises a pulse rate between 0.5 Hz and 1200 Hz and a pulse width between 10 microseconds and 5000 microseconds.

24. The medical trial stimulation system of claim 23, further comprising the electrode coupled to the stimulation generator.

25. The medical trial stimulation system of claim 23, wherein the electrode is disposed on a lead.

26. The medical trial stimulation system of claim 25, wherein the external trial electrical stimulator further comprises a connector configured to electrically couple the stimulation generator and the lead.

27. The medical trial stimulation system of claim 25, wherein the external trial electrical stimulator is configured to automatically cease stimulation therapy when the lead is disconnected from the stimulation generator.

28. The medical trial stimulation system of claim 25, wherein the remote controller is configured to automatically detect a type of the lead connected to the external trial electrical stimulator.

29. The medical trial stimulation system of claim 23, wherein the button, when engaged, causes power to be delivered to the telemetry module to enable wireless communication between the remote controller and external trial electrical stimulator.

30. The medical trial stimulation system of claim 23, wherein, when in the low power mode, the external trial electrical stimulator is not delivering stimulation therapy.

31. The medical trial stimulation system of claim 23, wherein the button, when engaged, causes the external trial electrical stimulator to exit the low power mode and enter the operational power mode to enable programming of the external trial electrical stimulator.

32. The medical trial stimulation system of claim 23, wherein, when in the low power mode, a power management module of the external trial electrical stimulator is powered on while at least one of the telemetry module and the stimulation generator is powered off, and wherein in the operational power mode the external trial electrical stimulator provides power to at least one of the telemetry module and the stimulation generator.

33. An external trial electrical stimulator comprising:
    a telemetry module;
    a housing with a single user control, the single user control comprising one of a button, a rocker switch, a slider switch, or a rotary dial switch, wherein the single user control, when activated, causes the external trial electrical stimulator to: (i) exit a low power mode, in which the external trial electrical stimulator is consuming low power, and enter an operational power mode and (ii) be capable of wireless communication with a remote controller via the telemetry module;

a stimulation generator disposed within the housing and being responsive to the remote controller; and a connector configured to electrically couple the stimulation generator and a lead that is configured to be at least partially implanted, the stimulation generator configured to, after receipt of a wireless communication from the remote controller, generate an electrical signal for stimulation therapy via the lead, wherein the electrical signal comprises a pulse rate between 0.5 Hz and 1200 Hz and a pulse width between 10 microseconds and 5000 microseconds.

34. The external trial electrical stimulator of claim 33, wherein, when in the low power mode, the external trial electrical stimulator not delivering stimulation therapy.

35. The external trial electrical stimulator of claim 33, wherein, when in the low power mode, the external trial electrical stimulator is disabled from wireless communication with the remote controller, and wherein in the operational power mode the external trial electrical stimulator is enabled for wireless communication with the remote controller.

36. The external trial electrical stimulator of claim 33, wherein, when in the low power mode, the external trial electrical stimulator does not provide power to the telemetry module, and wherein in the operational power mode the external trial electrical stimulator does provide power to the telemetry module.

37. The external trial electrical stimulator of claim 33, wherein, when in the low power mode, the external trial electrical stimulator does not provide power to the stimulation generator, and wherein in the operational power mode the external trial electrical stimulator does provide power to the stimulation generator.

38. The external trial electrical stimulator of claim 33, wherein, when in the low power mode, a power management module of the external trial electrical stimulator is powered on while at least one of the telemetry module and the stimulation generator is powered off, and wherein the single user control, when activated, causes the external trial electrical stimulator to exit the low power mode and enter the operational power mode by at least initiating delivery of power to at least one of the telemetry module and the stimulation generator.

39. The external trial electrical stimulator of claim 33, wherein the remote controller is a physician programmer.

40. The external trial electrical stimulator of claim 39, wherein the external trial electrical stimulator is configured to receive stimulation therapy instructions, for the stimulation generator, from the physician programmer to program the external trial electrical stimulator when the external trial electrical stimulator is in the operational power mode.

* * * * *